United States Patent
Gerber et al.

(10) Patent No.: US 11,806,457 B2
(45) Date of Patent: *Nov. 7, 2023

(54) PERITONEAL DIALYSIS ADEQUACY MEAUREMENTS

(71) Applicant: Medtronic, Inc., Minneapolis, MN (US)

(72) Inventors: Martin T. Gerber, Maple Grove, MN (US); Christopher M. Hobot, Rogers, MN (US)

(73) Assignee: Mozarc Medical US LLC, Minneapolis, MN (US)

( * ) Notice: Subject to any disclaimer, the term of this patent is extended or adjusted under 35 U.S.C. 154(b) by 627 days.

This patent is subject to a terminal disclaimer.

(21) Appl. No.: 16/674,532

(22) Filed: Nov. 5, 2019

(65) Prior Publication Data

US 2020/0155748 A1 May 21, 2020

Related U.S. Application Data

(60) Provisional application No. 62/768,320, filed on Nov. 16, 2018.

(51) Int. Cl.
  *A61M 1/28* (2006.01)
  *G16H 20/40* (2018.01)
  *A61B 5/20* (2006.01)

(52) U.S. Cl.
  CPC .......... *A61M 1/285* (2013.01); *G16H 20/40* (2018.01); *A61B 5/201* (2013.01); *A61M 2205/3303* (2013.01); *A61M 2205/3334* (2013.01); *A61M 2205/50* (2013.01); *A61M 2230/20* (2013.01); *A61M 2230/201* (2013.01)

(58) Field of Classification Search
  CPC .......... A61M 1/285; A61M 2205/3303; A61M 2205/3334
  See application file for complete search history.

(56) References Cited

U.S. PATENT DOCUMENTS

| | | |
|---|---|---|
| 2,002 A | 3/1841 | Rider |
| 3,602,222 A | 8/1971 | Herndon |
| 3,608,729 A | 9/1971 | Haselden |

(Continued)

FOREIGN PATENT DOCUMENTS

| | | |
|---|---|---|
| CN | 1273535 | 11/2000 |
| CN | 1643368 A | 7/2005 |

(Continued)

OTHER PUBLICATIONS

Brophy, Donald F., and Bruce A. Mueller. "Automated peritoneal dialysis: new implications for pharmacists." Annals of Pharmacotherapy 31.6 (1997): 756-764. (Year: 1997).*

(Continued)

*Primary Examiner* — Jenna Zhang

(74) *Attorney, Agent, or Firm* — Hahn & Associates

(57) ABSTRACT

The invention relates to devices, systems, and methods for measuring dialysis adequacy in patients undergoing peritoneal dialysis treatment. The devices, systems, and methods use one or more flow sensors and one or more solute sensors to measure the concentration of a uremic solute and volume of the peritoneal dialysate removed from the patient, and to calculate the dialysis adequacy based on the measured peritoneal dialysate concentration and volume.

24 Claims, 3 Drawing Sheets

(56) References Cited

U.S. PATENT DOCUMENTS

| | | | |
|---|---|---|---|
| 3,669,878 A | 6/1972 | Marantz | |
| 3,669,880 A | 6/1972 | Marantz | |
| 3,730,183 A | 5/1973 | Goldsmith | |
| 3,850,835 A | 11/1974 | Marantz | |
| 3,884,808 A | 5/1975 | Scott | |
| 3,989,622 A | 11/1976 | Marantz | |
| 3,989,625 A | 11/1976 | Mason | |
| 4,060,485 A | 11/1977 | Eaton | |
| 4,371,385 A | 2/1983 | Johnson | |
| 4,374,382 A | 2/1983 | Markowitz | |
| 4,381,999 A | 5/1983 | Boucher | |
| 4,460,555 A | 7/1984 | Thompson | |
| 4,556,063 A | 12/1985 | Thompson | |
| 4,562,751 A | 1/1986 | Nason | |
| 4,581,141 A | 4/1986 | Ash | |
| 4,650,587 A | 3/1987 | Polak | |
| 4,678,408 A | 7/1987 | Mason | |
| 4,685,903 A | 8/1987 | Cable | |
| 4,750,494 A | 6/1988 | King | |
| 4,799,493 A | 1/1989 | DuFault | |
| 4,826,663 A | 5/1989 | Alberti | |
| 4,828,693 A | 5/1989 | Lindsay | |
| 4,976,683 A * | 12/1990 | Gauthier | A61M 1/28 604/27 |
| 5,032,265 A | 7/1991 | Jha | |
| 5,080,653 A | 1/1992 | Voss | |
| 5,092,886 A | 3/1992 | Dobos-Hardy | |
| 5,097,122 A | 3/1992 | Coiman | |
| 5,127,404 A | 7/1992 | Wyborny | |
| 5,284,470 A | 2/1994 | Beltz | |
| 5,302,288 A | 4/1994 | Meidl | |
| 5,305,745 A | 4/1994 | Zacouto | |
| 5,318,750 A | 6/1994 | Lascombes | |
| 5,468,388 A | 11/1995 | Goddard | |
| 5,507,723 A | 4/1996 | Keshaviah | |
| 5,643,201 A | 7/1997 | Peabody | |
| 5,651,893 A | 7/1997 | Kenley | |
| 5,683,432 A | 11/1997 | Goedeke | |
| 5,744,031 A | 4/1998 | Bene | |
| 5,762,782 A | 6/1998 | Kenley | |
| 5,819,007 A | 10/1998 | Elghazzawi | |
| 5,849,179 A * | 12/1998 | Emerson | A61M 1/3609 210/96.2 |
| 5,902,336 A | 5/1999 | Mishkin | |
| 5,944,684 A | 8/1999 | Roberts | |
| 5,987,352 A | 11/1999 | Klein | |
| 6,048,732 A | 4/2000 | Anslyn | |
| 6,052,622 A | 4/2000 | Holmstrom | |
| 6,058,331 A | 5/2000 | King | |
| 6,156,002 A | 12/2000 | Polaschegg | |
| 6,230,059 B1 | 5/2001 | Duffin | |
| 6,248,093 B1 | 6/2001 | Moberg | |
| 6,254,567 B1 | 7/2001 | Treu | |
| 6,321,101 B1 | 11/2001 | Holmstrom | |
| 6,362,591 B1 | 3/2002 | Moberg | |
| 6,363,279 B1 | 3/2002 | Ben-Haim | |
| 6,505,075 B1 | 1/2003 | Weiner | |
| 6,554,798 B1 | 4/2003 | Mann | |
| 6,555,986 B2 | 4/2003 | Moberg | |
| 6,589,229 B1 | 7/2003 | Connelly | |
| 6,602,399 B1 | 8/2003 | Fromherz | |
| 6,609,023 B1 | 8/2003 | Fischell | |
| 6,627,164 B1 | 9/2003 | Wong | |
| 6,645,191 B1 | 11/2003 | Knerr | |
| 6,676,608 B1 | 1/2004 | Keren | |
| 6,689,083 B1 | 2/2004 | Gelfand | |
| 6,706,007 B2 | 3/2004 | Gelfand | |
| 6,711,439 B1 | 3/2004 | Bradley | |
| 6,726,647 B1 | 4/2004 | Sternby | |
| 6,780,322 B1 | 8/2004 | Bissler | |
| 6,818,196 B2 | 11/2004 | Wong | |
| 6,878,283 B2 | 4/2005 | Thompson | |
| 6,887,214 B1 | 5/2005 | Levin | |
| 6,890,315 B1 | 5/2005 | Levin | |
| 6,960,179 B2 | 11/2005 | Gura | |
| 7,074,332 B2 | 7/2006 | Summerton | |
| 7,077,819 B1 | 7/2006 | Goldau | |
| 7,131,956 B1 | 11/2006 | Pirazzoli | |
| 7,175,809 B2 | 2/2007 | Gelfand | |
| 7,207,946 B2 | 4/2007 | Sirokman | |
| 7,208,092 B2 | 4/2007 | Micheli | |
| 7,276,042 B2 | 10/2007 | Polaschegg | |
| 7,399,289 B2 | 7/2008 | Gelfand | |
| 7,404,799 B1 | 7/2008 | Koh | |
| 7,500,958 B2 | 3/2009 | Asbrink | |
| 7,566,432 B2 | 7/2009 | Wong | |
| 7,575,564 B2 | 8/2009 | Childers | |
| 7,610,086 B1 | 10/2009 | Ke | |
| 7,674,231 B2 | 3/2010 | McCombie | |
| 7,704,361 B2 | 4/2010 | Garde | |
| 7,736,507 B2 | 6/2010 | Wong | |
| 7,744,553 B2 | 6/2010 | Kelly | |
| 7,754,852 B2 | 7/2010 | Burnett | |
| 7,756,572 B1 | 7/2010 | Fard | |
| 7,775,983 B2 | 8/2010 | Zhang | |
| 7,775,986 B2 | 8/2010 | Roeher | |
| 7,776,210 B2 | 8/2010 | Rosenbaum | |
| 7,785,463 B2 | 8/2010 | Bissler | |
| 7,794,141 B2 | 9/2010 | Perry | |
| 7,850,635 B2 | 12/2010 | Polaschegg | |
| 7,857,976 B2 | 12/2010 | Bissler | |
| 7,867,214 B2 | 1/2011 | Childers | |
| 7,896,831 B2 | 3/2011 | Sternby | |
| 7,922,686 B2 | 4/2011 | Childers | |
| 7,922,911 B2 | 4/2011 | Micheli | |
| 7,947,179 B2 | 5/2011 | Rosenbaum | |
| 7,955,291 B2 | 6/2011 | Sternby | |
| 7,967,022 B2 | 6/2011 | Grant | |
| 7,981,082 B2 | 7/2011 | Wang | |
| 8,000,000 B2 | 8/2011 | Greenberg | |
| 8,034,161 B2 | 10/2011 | Gura | |
| 8,070,709 B2 | 12/2011 | Childers | |
| 8,096,969 B2 | 1/2012 | Roberts | |
| 8,105,260 B2 | 1/2012 | Tonelli | |
| 8,183,046 B2 | 5/2012 | Lu | |
| 8,187,250 B2 | 5/2012 | Roberts | |
| 8,197,439 B2 | 6/2012 | Wang | |
| 8,202,241 B2 | 6/2012 | Karakama | |
| 8,246,826 B2 | 8/2012 | Wilt | |
| 8,273,049 B2 | 9/2012 | Demers | |
| 8,282,828 B2 | 10/2012 | Wallenas | |
| 8,292,594 B2 | 10/2012 | Tracey | |
| 8,313,642 B2 | 11/2012 | Yu | |
| 8,317,492 B2 | 11/2012 | Demers | |
| 8,357,113 B2 | 1/2013 | Childers | |
| 8,366,316 B2 | 2/2013 | Kamen | |
| 8,366,655 B2 | 2/2013 | Kamen | |
| 8,404,091 B2 | 3/2013 | Ding | |
| 8,409,441 B2 | 4/2013 | Wilt | |
| 8,496,809 B2 | 7/2013 | Roger | |
| 8,499,780 B2 | 8/2013 | Wilt | |
| 8,500,676 B2 | 8/2013 | Jansson | |
| 8,512,271 B2 | 8/2013 | Moissl | |
| 8,518,260 B2 | 8/2013 | Raimann | |
| 8,521,482 B2 | 8/2013 | Akonur | |
| 8,535,525 B2 | 9/2013 | Heyes | |
| 8,560,510 B2 | 10/2013 | Brueggerhoff | |
| 8,580,112 B2 | 11/2013 | Updyke | |
| 8,597,227 B2 | 12/2013 | Childers | |
| 8,696,626 B2 | 4/2014 | Kirsch | |
| 8,903,492 B2 | 12/2014 | Soykan | |
| 8,926,542 B2 | 1/2015 | Gerber | |
| 9,907,897 B2 | 3/2018 | Burbank | |
| 10,046,100 B2 | 8/2018 | Burbank | |
| 2002/0016550 A1 | 2/2002 | Sweeney | |
| 2002/0042561 A1 | 4/2002 | Schulman | |
| 2002/0112609 A1 | 8/2002 | Wong | |
| 2003/0028089 A1 | 2/2003 | Galley | |
| 2003/0069481 A1 | 4/2003 | Hervy | |
| 2003/0080059 A1 | 5/2003 | Peterson | |
| 2003/0097086 A1 | 5/2003 | Gura | |
| 2003/0105435 A1 | 6/2003 | Taylor | |
| 2003/0113931 A1 | 6/2003 | Pan | |
| 2003/0114787 A1 | 6/2003 | Gura | |

(56) References Cited

U.S. PATENT DOCUMENTS

| | | |
|---|---|---|
| 2003/0187479 A1 | 10/2003 | TranThong |
| 2004/0019312 A1 | 1/2004 | Childers |
| 2004/0068219 A1 | 4/2004 | Summerton |
| 2004/0099593 A1 | 5/2004 | DePaolis |
| 2004/0147900 A1 | 7/2004 | Polaschegg |
| 2004/0168969 A1 | 9/2004 | Sternby |
| 2004/0215090 A1 | 10/2004 | Erkkila |
| 2005/0065760 A1 | 3/2005 | Murtfeldt |
| 2005/0113796 A1 | 5/2005 | Taylor |
| 2005/0126961 A1 | 6/2005 | Bissler |
| 2005/0131331 A1 | 6/2005 | Kelly |
| 2005/0126998 A1 | 7/2005 | Childers |
| 2005/0150832 A1 | 7/2005 | Tsukamoto |
| 2005/0214863 A1 | 9/2005 | McDevitt |
| 2005/0234354 A1 | 10/2005 | Rowlandson |
| 2005/0234357 A1 | 10/2005 | Xue |
| 2005/0234381 A1 | 10/2005 | Niemetz |
| 2005/0234534 A1 | 10/2005 | Rowlandson |
| 2005/0236330 A1 | 10/2005 | Nier |
| 2005/0265895 A1 | 12/2005 | Kopelman |
| 2005/0274658 A1 | 12/2005 | Rosenbaum |
| 2006/0025661 A1 | 2/2006 | Sweeney |
| 2006/0025748 A1 | 2/2006 | Ye |
| 2006/0058731 A1 | 3/2006 | Burnett |
| 2006/0191850 A1 | 8/2006 | Bosetto |
| 2006/0195064 A1 | 8/2006 | Plahey |
| 2006/0217771 A1 | 9/2006 | Soykan |
| 2006/0226079 A1 | 10/2006 | Mori |
| 2006/0241709 A1 | 10/2006 | Soykan |
| 2006/0247548 A1 | 11/2006 | Sarkar |
| 2006/0264894 A1 | 11/2006 | Moberg |
| 2007/0007208 A1 | 1/2007 | Brugger |
| 2007/0038138 A1 | 2/2007 | Gill |
| 2007/0066928 A1 | 3/2007 | Lannoy |
| 2007/0073168 A1 | 3/2007 | Zhang |
| 2007/0138011 A1 | 6/2007 | Hofmann |
| 2007/0161113 A1 | 7/2007 | Ash |
| 2007/0175827 A1 | 8/2007 | Wariar |
| 2007/0179431 A1 | 8/2007 | Roberts |
| 2007/0213653 A1 | 9/2007 | Childers |
| 2007/0215545 A1 | 9/2007 | Bissler |
| 2007/0255250 A1 | 11/2007 | Moberg |
| 2007/0276270 A1 | 11/2007 | Tran |
| 2008/0006570 A1 | 1/2008 | Gura |
| 2008/0015487 A1 | 1/2008 | Szamosfalvi et al. |
| 2008/0021337 A1 | 1/2008 | Li |
| 2008/0053905 A9 | 3/2008 | Brugger |
| 2008/0067132 A1 | 3/2008 | Ross |
| 2008/0093276 A1 | 4/2008 | Roger |
| 2008/0200866 A1 | 8/2008 | Prisco |
| 2008/0215247 A1 | 9/2008 | Tonelli |
| 2008/0253427 A1 | 10/2008 | Kamen |
| 2009/0020471 A1 | 1/2009 | Tsukamoto |
| 2009/0036825 A1 | 2/2009 | Petersen |
| 2009/0101577 A1 | 4/2009 | Fulkerson |
| 2009/0124869 A1 | 5/2009 | Hu |
| 2009/0124963 A1 | 5/2009 | Hogard |
| 2009/0127193 A1 | 5/2009 | Updyke |
| 2009/0171261 A1 | 7/2009 | Sternby |
| 2009/0264776 A1 | 10/2009 | Vardy |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0010425 A1 | 1/2010 | Yu |
| 2010/0010427 A1* | 1/2010 | Yu .................. A61M 1/1603 604/29 |
| 2010/0010429 A1 | 1/2010 | Childers |
| 2010/0042035 A1 | 2/2010 | Moissl |
| 2010/0076398 A1 | 3/2010 | Scheurer |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0113891 A1 | 5/2010 | Barrett |
| 2010/0114012 A1 | 5/2010 | Sandford |
| 2010/0137693 A1 | 6/2010 | Porras |
| 2010/0137782 A1 | 6/2010 | Jansson |
| 2010/0168546 A1 | 7/2010 | Kamath |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0264086 A1 | 10/2010 | Noack |
| 2010/0312172 A1 | 12/2010 | Hoffman |
| 2011/0017665 A1 | 1/2011 | Updyke |
| 2011/0048949 A1 | 3/2011 | Ding et al. |
| 2011/0066006 A1 | 3/2011 | Banet |
| 2011/0066043 A1 | 3/2011 | Banet |
| 2011/0071465 A1 | 3/2011 | Wang |
| 2011/0077574 A1 | 3/2011 | Sigg |
| 2011/0079558 A1 | 4/2011 | Raimann |
| 2011/0081728 A1 | 4/2011 | Putnam |
| 2011/0087187 A1 | 4/2011 | Beck |
| 2011/0100909 A1 | 5/2011 | Stange |
| 2011/0106003 A1 | 5/2011 | Childers |
| 2011/0130666 A1 | 6/2011 | Dong |
| 2011/0137136 A1 | 6/2011 | Kotanko |
| 2011/0141116 A1 | 6/2011 | Dalesch |
| 2011/0144570 A1 | 6/2011 | Childers |
| 2011/0184340 A1 | 7/2011 | Tan |
| 2011/0208105 A1 | 8/2011 | Brandl |
| 2011/0272337 A1 | 11/2011 | Palmer |
| 2011/0301447 A1 | 12/2011 | Park |
| 2011/0301472 A1 | 12/2011 | Grober |
| 2012/0016228 A1 | 1/2012 | Kroh |
| 2012/0029937 A1* | 2/2012 | Neftel .................. A61M 1/3609 705/2 |
| 2012/0083729 A1 | 4/2012 | Childers |
| 2012/0085707 A1 | 4/2012 | Beiriger |
| 2012/0115248 A1 | 5/2012 | Ansyln |
| 2012/0135396 A1 | 5/2012 | McDevitt |
| 2012/0181230 A1 | 7/2012 | Kloeffel |
| 2012/0220528 A1 | 8/2012 | Van Antwerp |
| 2012/0258545 A1 | 10/2012 | Ash |
| 2012/0258546 A1 | 10/2012 | Marran |
| 2012/0259276 A1 | 10/2012 | Childers |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0283581 A1 | 11/2012 | Olde et al. |
| 2012/0303079 A1 | 11/2012 | Mahajan et al. |
| 2013/0037465 A1 | 2/2013 | Heyes |
| 2013/0062265 A1 | 3/2013 | Balschat |
| 2013/0116578 A1 | 5/2013 | QiAn |
| 2013/0158461 A1 | 6/2013 | Sasaki et al. |
| 2013/0168316 A1 | 7/2013 | Noguchi |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228517 A1 | 9/2013 | Roger |
| 2013/0231607 A1 | 9/2013 | Roger |
| 2013/0248426 A1 | 9/2013 | Pouchoulin |
| 2013/0274642 A1 | 10/2013 | Soykan |
| 2013/0324915 A1 | 12/2013 | (Krensky) Britton |
| 2013/0330208 A1 | 12/2013 | Ly |
| 2013/0331774 A1 | 12/2013 | Farrell |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |

(56) References Cited

U.S. PATENT DOCUMENTS

| | | | |
|---|---|---|---|
| 2014/0110341 A1 | 4/2014 | White | |
| 2014/0158538 A1 | 6/2014 | Collier | |
| 2014/0158588 A1 | 6/2014 | Pudil | |
| 2014/0158623 A1 | 6/2014 | Pudil | |
| 2014/0190876 A1 | 7/2014 | Meyer | |
| 2014/0190886 A1* | 7/2014 | Pudil | A61M 1/1696 210/93 |
| 2014/0216250 A1 | 8/2014 | Meyer | |
| 2014/0217028 A1 | 8/2014 | Pudil | |
| 2014/0217029 A1 | 8/2014 | Meyer | |
| 2014/0217030 A1 | 8/2014 | Meyer | |
| 2014/0220699 A1 | 8/2014 | Pudil | |
| 2014/0314625 A1 | 10/2014 | Clift | |
| 2015/0032023 A1 | 1/2015 | Soykan | |
| 2015/0080682 A1 | 3/2015 | Gerber | |
| 2015/0088047 A1 | 3/2015 | Gerber | |
| 2015/0141512 A1 | 5/2015 | Kizhakkedathu et al. | |
| 2015/0144539 A1 | 5/2015 | Pudil | |
| 2015/0148697 A1 | 5/2015 | Burnes | |
| 2015/0149096 A1 | 5/2015 | Soykan | |
| 2015/0250427 A1 | 9/2015 | Soykan | |
| 2015/0343126 A1 | 12/2015 | Merchant | |
| 2015/0352269 A1 | 12/2015 | Gerber | |
| 2015/0367054 A1 | 12/2015 | Gerber | |
| 2016/0018347 A1 | 1/2016 | Drbal et al. | |
| 2016/0023467 A1 | 1/2016 | Smith | |
| 2016/0206801 A1 | 7/2016 | Gerber | |
| 2016/0331884 A1 | 11/2016 | Sigg | |
| 2018/0043080 A1 | 2/2018 | Gerber et al. | |
| 2019/0358387 A1* | 11/2019 | Elbadry | A61M 1/3663 |

FOREIGN PATENT DOCUMENTS

| | | |
|---|---|---|
| CN | 101193667 | 6/2008 |
| CN | 101300476 A | 11/2008 |
| CN | 202048893 | 3/2011 |
| CN | 103037917 | 4/2013 |
| CN | 103619372 | 3/2014 |
| CN | 104833635 A | 8/2015 |
| CN | 104884102 | 9/2015 |
| CN | 105008893 B | 10/2015 |
| DE | 3224823 | 1/1984 |
| EP | 266795 A2 | 11/1987 |
| EP | 0402505 | 12/1990 |
| EP | 0272414 | 10/1991 |
| EP | 0330892 | 7/1994 |
| EP | 1124599 | 5/2000 |
| EP | 1175238 | 11/2000 |
| EP | 2308526 | 10/2003 |
| EP | 1364666 A1 | 11/2003 |
| EP | 1523347 | 1/2004 |
| EP | 1523350 | 1/2004 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |
| EP | 1592494 B1 | 6/2009 |
| EP | 2100553 A1 | 9/2009 |
| EP | 2398529 | 11/2010 |
| EP | 2575827 A2 | 12/2010 |
| EP | 2100553 | 8/2011 |
| EP | 2576453 A2 | 12/2011 |
| EP | 2701580 | 11/2012 |
| EP | 2701595 | 11/2012 |
| EP | 1345856 B1 | 3/2013 |
| EP | 2344220 B1 | 4/2013 |
| EP | 1351756 | 7/2013 |
| EP | 2190498 | 7/2013 |
| EP | 2701596 | 3/2014 |
| EP | 1582226 | 1/2016 |
| JP | S551980138462 | 10/1980 |
| JP | S63-143077 | 11/1987 |
| JP | 2002533170 | 10/2002 |
| JP | 2002542900 | 12/2002 |
| JP | 2003235965 | 8/2003 |
| JP | 2005-533573 | 11/2005 |
| JP | 5099464 | 10/2012 |
| WO | 1995003839 | 2/1995 |
| WO | WO1999006082 | 2/1999 |
| WO | 9937342 | 7/1999 |
| WO | 0057935 | 10/2000 |
| WO | WO2000057935 A1 | 10/2000 |
| WO | 200066197 A1 | 11/2000 |
| WO | 2000066197 | 11/2000 |
| WO | 200170307 A1 | 9/2001 |
| WO | 2001085295 A2 | 9/2001 |
| WO | 0185295 A2 | 11/2001 |
| WO | 1085295 | 11/2001 |
| WO | 2002013691 | 2/2002 |
| WO | 2003043677 A2 | 5/2003 |
| WO | 2003043680 | 5/2003 |
| WO | 2003051422 A2 | 6/2003 |
| WO | 2004008826 | 1/2004 |
| WO | 2004009156 | 1/2004 |
| WO | 2004009158 | 1/2004 |
| WO | 2004030716 A2 | 4/2004 |
| WO | 2004030717 A2 | 4/2004 |
| WO | 2004064616 A2 | 8/2004 |
| WO | 2005033701 | 4/2005 |
| WO | 2005061026 | 7/2005 |
| WO | 2005123230 A2 | 12/2005 |
| WO | 2006011009 | 2/2006 |
| WO | 2006017446 | 2/2006 |
| WO | 2007038347 | 4/2007 |
| WO | 2007089855 A2 | 8/2007 |
| WO | WO2009094035 A1 | 1/2008 |
| WO | 2008037410 | 4/2008 |
| WO | 2009026603 | 12/2008 |
| WO | 2009024566 | 2/2009 |
| WO | 2009026603 A1 | 3/2009 |
| WO | 2009061608 | 5/2009 |
| WO | 2009094184 | 7/2009 |
| WO | 2009157877 A1 | 12/2009 |
| WO | 2009157878 A1 | 12/2009 |
| WO | WO2009154955 A2 | 12/2009 |
| WO | WO 20100002830 | 1/2010 |
| WO | 2010024963 | 3/2010 |
| WO | 2010028860 | 3/2010 |
| WO | 2010028860 A1 | 3/2010 |
| WO | 2010033314 | 3/2010 |
| WO | 2010033699 | 3/2010 |
| WO | 2010077851 | 7/2010 |
| WO | 2010096659 | 10/2010 |
| WO | 2010121820 | 10/2010 |
| WO | 2011025705 A1 | 3/2011 |
| WO | 2011026645 | 3/2011 |
| WO | WO2013022760 A1 | 8/2011 |
| WO | WO 2011/132046 | 10/2011 |
| WO | 2011137693 | 11/2011 |
| WO | WO2011161056 | 12/2011 |
| WO | 2012042323 | 4/2012 |
| WO | 2012050781 | 4/2012 |
| WO | 2012051996 | 4/2012 |
| WO | 2012073420 | 7/2012 |
| WO | WO 2012/129501 | 9/2012 |
| WO | 2012148781 | 11/2012 |
| WO | 2012148786 | 11/2012 |
| WO | 2012148787 A1 | 11/2012 |
| WO | 2012148789 | 11/2012 |
| WO | 2012162515 A2 | 11/2012 |
| WO | 20120277551 | 11/2012 |
| WO | WO2012148788 A1 | 11/2012 |
| WO | 2012148784 | 12/2012 |
| WO | 2012172398 | 12/2012 |
| WO | 2013019179 A1 | 2/2013 |
| WO | 2013019994 A2 | 2/2013 |
| WO | 2013025844 | 2/2013 |
| WO | 2013028809 A3 | 2/2013 |
| WO | 2013101292 | 7/2013 |
| WO | 2013103607 A1 | 7/2013 |
| WO | 2013103906 | 7/2013 |

(56) References Cited

FOREIGN PATENT DOCUMENTS

| WO | 2013110906 | | 8/2013 | |
| --- | --- | --- | --- | --- |
| WO | 2013110919 | | 8/2013 | |
| WO | 2013114063 | A1 | 8/2013 | |
| WO | 2013121162 | A1 | 8/2013 | |
| WO | 2013140346 | | 9/2013 | |
| WO | 2013141896 | | 9/2013 | |
| WO | 2013101292 | A3 | 10/2013 | |
| WO | 14066254 | | 5/2014 | |
| WO | 14066255 | | 5/2014 | |
| WO | 14077082 | | 5/2014 | |
| WO | 2014121162 | | 8/2014 | |
| WO | 2014121163 | | 8/2014 | |
| WO | 2014121167 | | 8/2014 | |
| WO | 2014121169 | | 8/2014 | |
| WO | WO2014121161 | | 8/2014 | |
| WO | WO2015081221 | A1 | 6/2015 | |
| WO | WO 20160080883 | | 5/2016 | |
| WO | WO 2017/176701 | | 10/2017 | |
| WO | WO-2018142406 | A1 * | 8/2018 | ............. A61M 1/28 |

OTHER PUBLICATIONS

International Search Report for PCT/US2019/061670 date of completion is Dec. 25, 2019 (13 pages).
Dejardin, et al., Intraperitoneal pressure in PD patients: relationship to intraperitoneal volume, body size and PD-related complications, Nephrol Dial Transplant. May 2007;22(5):1437-44.
[NPL105] Brynda, et. al., The detection of toman 2-microglcbuiin by grating coupler immunosensor with three dimensional antibody networks. Biosensors & Bioelectronics, 1999, 363-368, 14(4).
[NPL10] Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
[NPL111] Zhong, et. al., Miniature urea sensor based on H(+)-ion sensitive field effect transistor and its application in clinical analysis, Chin. J. Biotechnol., 1992, 57-65. 8(1).
[NPL119] PCT/US2012/034331, International Search Report and Written Opinion dated Jul. 9, 2012.
[NPL121] Roberts M, The regenerative dialysis (REDY) sorbent system. Nephrology, 1998, 275-278:4.
[NPL138] U.S. Appl. No. 61/480,544.
[NPL139] U.S. Appl. No. 61/480,541, filed Apr. 29, 2011.
[NPL142] Hemametrics, Crit-Line Hematocrit Accuracy, 2003, 1-5, vol. 1, Tech Note No. 11 (Rev. D).
[NPL144] Weissman, S., et al., Hydroxyurea-induced hepatitis in human immunodeficiency virus-positive patients. Clin. Infec. Dis, (Jul. 29, 1999): 223-224.
[NPL146] PCT/US2012/034334, International Search Report, dated Jul. 6, 2012.
[NPL147] PCT/US2012/034335, International Search Report, dated Sep. 5, 2012.
[NPL148] PCT/US/2012/034327, International Search Report, dated Aug. 13, 2013.
[NPL149] PCT/US/2012/034329, International Search Report, dated Dec. 3, 2012.
[NPL14] Foley, et al., Long Interdialytic Interval and Martality among Patients Receiving Hemodialysis, N Engl Jml Med. 2011:365(12):1099-1107.
[NPL15] PCT International Search Report from International Application No. PCT/US2014/067650, dated Nov. 27, 2013.
[NPL169] Wang, Fundamentals of intrathoracic impedance monitoring in heart failure, Am. J. Cardiology, 2007, 3G-10G: Suppl.
[NPL16] PCT/US2014/067650 International Search Report Written Opinion dated Mar. 9, 2015.
[NPL170] Bleyer, et al., Kidney International. Jun. 2006; 69(12):2268-2273.
[NPL176] Bleyer, et. al., Sudden and cardiac death rated in hemodialysis patients, Kidney International. 1999, 1553-1559: 55.

[NPL180] PCT/US2012/034335, International Preliminary Report on Patentability, dated Nov. 7, 2013.
[NPL181] PCT/US2012/034303, Internationa Search Report, dated Jul. 6, 2013.
[NPL186] PCT/US2012/034332, Internatonal Preliminary Report on Patentability, dated Oct. 29, 2013.
[NPL187] PCT/US2012/034333, International Preliminary Report on Patentability, dated Oct. 29, 2013.
[NPL188] PCT/US2012/034333, International Search Report, dated Aug. 29, 2012.
[NPL188] PCT/US2012/034333, International Search Report, dated Aug. 29, 2013.
[NPL195] PCT/US2012/034327, International Preliminary Report on Patentability, dated Oct. 29, 2013.
[NPL197] PCT/US2012/034330, International Preliminary Report on Patentability, dated Oct. 29, 2013.
[NPL205] Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
[NPL217] U.S. Appl. No. 13/757,722, filed Feb. 1, 2013.
[NPL218] U.S. Appl. No. 13/757,794, filed Feb. 2, 2012.
[NPL219] U.S. Appl. No. 13/791,755, filed Mar. 8, 2013.
[NPL21] U.S. Appl. No. 13/424,479, filed Nov. 1, 2012.
[NPL220] U.S. Appl. No. 13/757,792, filed Feb. 2, 2013.
[NPL222] U.S. Appl. No. 13/757,794, filed Feb. 2, 2013.
[NPL227] U.S. Appl. No. 13/837,287, filed Mar. 15, 2013.
[NPL22] U.S. Appl. No. 13/424,429, filed Nov. 1, 2012.
[NPL230] Redfield, et. al., Restoration of renal response to atria! natriuretic factor in experimental low-output heat failure, Am. J. Physiol., Oct. 1, 1989, R917-923:257.
[NPL231] Rogoza, et. al., Validation of A&D UA-767 device for the self-measurement of blood pressure, Blood Pressure Monitoring, 2000, 227-231, 5(4).
[NPL233] PCT/US2012/034329, International Preliminary Report on Patentability, dated Oct. 29, 2013.
[NPL234] Lima, et. al., An electrochemical sensor based on nanostructure hollsndite-type manganese oxide for detection of potassium ion, Sensors, Aug. 24, 2009, 6613-8625, 9.
[NPL235] Maclean, et, al., Effects of hindlimb contraction on pressor and muscle interstitial metabolite responses in the cat, J. App. Physiol., 1998, 1583-1592, 85(4).
[NPL237] U.S. Appl. No. 13/757,693, filed Feb. 1, 2013.
[NPL238] PCT Application, PCT/US20013/020404, filed Jan. 4, 2013.
[NPL23] U.S. Appl. No. 13/424,525.
[NPL240] U.S. Appl. No. 13/836,973, filed Mar. 15, 2013.
[NPL241] U.S. Appl. No. 14/259,655, filed Apr. 23, 2014.
[NPL242] U.S. Appl. No. 14/259,589, filed Apr. 23, 2014.
[NPL264] PCT/US2014/014357 International Search Report and Written Opinion dated May 19, 2014.
[NPL268] Ronco et al. 2008, Cardiorenal Syndrome, Journal American College Cardiology, 52:1527-1539, Abstract.
[NPL26] Overgaard, et. al., Activity-induced recovery of excitability in K+-depressed rat soleus muscle, Am. J. p. 280: R48-R55, Jan. 1, 2001.
[NPL27] Overgaard. et. al., Relations between excitability and contractility in rate soleusmuscle: role of the NA+-K+ pump and NA+-K-S gradients. Journal of Physiology, 1999, 215-225, 518(1).
[NPL285] Zoccali, Pulmonary Congestion Predicts Cardiac Events and Mortality in ESRD, Clinical Epidemiology, J. Am Soc Nephrol 24:639-646, 2013.
[NPL306] Coast, et al. 1990, An approach to Cardiac Arrhythmia analysis Using Hidden Markov Models, IEEE Transactions On Biomedical Engineering. 1990, 37(9):826-835.
[NPL309] Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
[NPL310] U.S. Appl. No. 61/480,532.
[NPL311] U.S. Appl. No. 13/424,479.
[NPL312] U.S. Appl. No. 13/424,429, filed Nov. 1, 2012.
[NPL313] U.S. Appl. No. 13/424,525.

(56) References Cited

OTHER PUBLICATIONS

[NPL317] U.S. Appl. No. 61/480,530.
[NPL318] U.S. Appl. No. 61/480,528 dated Apr. 29, 2011.
[NPL322] Velasco, Optimal Fluid Control can Normalize Cardiovascular Risk Markers and Limit Left Ventricular Hypertrophy in Thrice Weekly Dialysis Patients, Hemodialysis Intenational, 16:465-472, 2012.
[NPL323] Whitman, CKD and Sudden Cardiac Death: Epidemiology, Mechanisms, and Therapeutic Approaches, J Am Soc Nephrol, 23:1929-1939, 2012.
[NPL324] Hall, Hospitalization for Congestive Heart Failure: United States, 2000-2010, NCHS Data Brief, No. 108, Oct. 2012.
[NPL325] Albert, Fluid Management Strategies in Heart Failure, Critical Care Nurse, 32:20-32, 2012.
[NPL326] PCT/US2014/065201 International Search Report dated May 26, 2015.
[NPL328] Genovesi, et al., Nephrology, Dialysis, Transplantation 2009; 24(8):2529-2536.
[NPL32] Secemsky, et. al., High prevalence of cardiac autonomic dysfunction and T-wave alternans in dialysis patients. Heart Rhythm, Apr. 2011, 592-598 : vol. 8, No. 4.
[NPL339] U.S. Appl. No. 13/424,517 IDS, filed Aug. 2, 2012.
[NPL340] U.S. Appl. No. 13/424,517, IDS filed Dec. 2, 2013.
[NPL35] Wei, et. al., Fullerene-cryptand coated piezoelectric crystal urea sensor based on urease, Analytica Chimica Acta, 2001,77-85:437.
[NPL376] Gambro AK 96 Dialysis Machine Operators Manual, Dec. 2012. p. 1-140.
[NPL376] Gambro AK 96 Dialysis Machine Operators Manual, Dec. 2012. p. 141-280.
[NPL376] Gambro AK 96 Dialysis Machine Operators Manual, Dec. 2012. p. 281-420.
[NPL376] Gambro AK 96 Dialysis Machine Operators Manual, Dec. 2012. p. 421-534.
[NPL37] U.S. Appl. No. 13/368,225, filed Feb. 7, 2012.
[NPL383] Leifer et al., A Study on the Temperature Variation of Rise Velocity for Large Clean Bubbles, J. Atmospheric & Oceanic Tech., vol. 17, pp. 1392-1402, Oct. 2000.
[NPL384] Talaia, Terminal Velocity of a Bubble Rise in a Liquid Column, World Acad. of Sci., Engineering & Tech., vol. 28, pp. 264-268, Published Jan. 1, 2007.
[NPL386] The FHN Trial Group. In-Center. Hemodialysis Six Times per Week versus Three Times per Week, New England Journal of Medicine, 2010 Abstract.
[NPL39] PCT/US2012/034332, International Search Report, dated Jul. 5, 2012.
[NPL46] Siegenthaler, et al., Pulmonary fluid status monitoring with intrathoracic impedance, Journal of Clinical Monitoring and Computing, 24:449-451, published Jan. 12, 2011.
[NPL477] Office Action in U.S. Appl. No. 13/757,792 dated Apr. 6, 2015.
[NPL47] U.S. Appl. No. 61/480,544.
[NPL483] Office Action in U.S. Appl. No. 13/424,525 dated Aug. 11, 2015.
[NPL486] Office Action in U.S. Appl. No. 13/424,525 dated Oct. 20, 2016.
[NPL494] John Wm Agar: Review: Understanding sorbent dialysis systems, Nephrology, vol. 15, No. 4, Jun. 1, 2010, pp. 406-411.
[NPL495] European Office Action in Application 12717020.7 dated Sep. 14, 2016.
[NPL500] Office Action in U.S. Appl. No. 14/554,272 dated Aug. 8, 2016.
[NPL501] Office Action in U.S. Appl. No. 13/424,467 dated Oct. 16, 2013.
[NPL502] Office Action in U.S. Appl. No. 13/424,467 dated Mar. 3, 2014.
[NPL503] Office Action in U.S. Appl. No. 13/424,490 dated Oct. 22, 2013.
[NPL504] Office Action in U.S. Appl. No. 13/424,490 dated Mar. 10, 2014.
[NPL505] Office Action in U.S. Appl. No. 13/424,490 dated Jul. 14, 2014.
[NPL506] Office Action in U.S. Appl. No. 13/424,490 dated Dec. 5, 2014.
[NPL507] Office Action in U.S. Appl. No. 13/424,525 dated Sep. 29, 2014.
[NPL508] Office Action in U.S. Appl. No. 13/424,525 dated May 6, 2015.
[NPL509] Office Action in U.S. Appl. No. 13/424,454 dated Oct. 17, 2013.
[NPL510] Office Action in U.S. Appl. No. 13/424,454 dated Mar. 10, 2014.
[NPL511] Office action in U.S. Appl. No. 13/424,429 dated Oct. 15, 2015.
[NPL512] Office Action in U.S. Appl. No. 12/571,127 dated Feb. 27, 2014.
[NPL513] Office Action in U.S. Appl. No. 12/571,127 dated Jul. 6, 2015.
[NPL514] Office Action in U.S. Appl. No. 12/571,127 dated Dec. 17, 2015.
[NPL521] Office Action in U.S. Appl. No. 14/554,338 dated Jun. 7, 2016.
[NPL522] Office Action in U.S. Appl. No. 14/554,338 dated Sep. 28, 2016.
[NPL524] Office Action in U.S. Appl. No. 13/424,429 dated Oct. 15, 2015.
[NPL525] Office Action in U.S. Appl. No. 12/571,127 dated Feb. 27, 2014.
[NPL526] Office Action in U.S. Appl. No. 12/571,127 dated Jul. 6, 2015.
[NPL527] Office Action in U.S. Appl. No. 12/571,127 dated Dec. 17, 2015.
[NPL539] Office Action in U.S. Appl. No. 12/571,127 dated Nov. 8, 2012.
[NPL540] Office Action in U.S. Appl. No. 14/554,338 dated Jun. 7, 2016.
[NPL541] Office Action in U.S. Appl. No. 14/554,338 dated Sep. 28, 2016.
[NPL542] Office Action in U.S. Appl. No. 14/554,272 dated Aug. 8, 2016.
[NPL543] Office Action in U.S. Appl. No. 13/424,479 dated Oct. 25, 2014.
[NPL545] Office Action in U.S. Appl. No. 14/566,686 dated Apr. 28, 2016.
[NPL547] Office Action in Chinese Application No. 201510511657.9 dated Dec. 28, 2016.
[NPL55] U.S. Appl. No. 13/424,454.
[NPL57] U.S. Appl. No. 13/424,467.
[NPL582] Office Action in U.S. Appl. No. 13/757,792 dated Apr. 6, 2015.
[NPL62] U.S. Appl. No. 13/424,533.
[NPL632] Lakerveld et al, Primary prevention of diabetes mellitus type 2 and cardiovascular diseases using a cognitive behavior program aimed at lifestyle changes in people at risk: Design of a randomized controlled trial, 2008, BMC Endocrine Disorders, 8(6): 1-19.
[NPL633] Gordhandas et al., Real-Time Extraction and Analysis of Key Morphological Features in the Electrocardiogram, for Data Compression and Clinical Decision Support, 2004, Computational Physiology, pp. 15-18.
[NPL671] European Office Action in Application 12717020.7 dated Dec. 11, 2015.
[NPL672] PCT/US2012/034331 International Preliminary Report on Patentability and Written Opinion dated Oct. 29, 2013.
[NPL674] Office Action in Chinese Application No. 201280020932.1 dated Jan. 7, 2015.
[NPL675] Office Action in Chinese Application No. 201280020932.1 dated Apr. 3, 2015.
[NPL67] U.S. Appl. No. 13/424,490.
[NPL68] U.S. Appl. No. 13/424,517.
[NPL693] PCT/US2012/034330, International Search Report and Written Opinion dated Aug. 28, 2012.

(56) References Cited

OTHER PUBLICATIONS

[NPL699] Office Action in Chinese Application No. 201280020937.4 dated Oct. 22, 2016.
[NPL700] Office Action in Japanese Application No. 2014-508434 dated Nov. 16, 2015.
[NPL701] Office Action in Japanese Application No. 2014-508434 dated Dec. 8, 2014.
[NPL702] Office Action in Japanese Application No. 2014-508434 dated Nov. 4, 2016.
[NPL703] Office Action in European Application No. 12717019.9 dated Feb. 16, 2017.
[NPL706] Office Action in Chinese Application No. 201510511657.9 dated May 10, 2017.
[NPL709] PCT/US2014/065201 International Preliminary Report on Patentability dated May 19, 2016.
[NPL727] Office Action in European Application No. EP 12717021.5 dated Feb. 3, 2017.
[NPL735] Office Action in Chinese Application No. 201510593695.3 dated Jul. 12, 2017.
[NPL748] Office Action in European Application No. EP 12719170.8 dated Jan. 14, 2015.
[NPL749] Office Action in Japanese Application No. JP 2014-508437 dated Dec. 8, 2014.
[NPL757] U.S. Appl. No. 60/650,497 dated Feb. 7, 2005.
[NPL81] U.S. Appl. No. 61/480,539 dated Apr. 29, 2011.
[NPL84] U.S. Appl. No. 61/480,535 dated Apr. 29, 2011.
[NPL90] Nedelkov, et. al., Design of buffer exchange surfaces and sensor chips for biosensor chip mass spectrometry, Proteomics, 2002, 441-446, 2(4).
[NPL] European Search Report App 14865374.4, dated Jun. 12, 2017.
[NPL] European Search Report for Application No. 14865128.4 dated Jun. 20, 2017.
[NPL] Green et al., Sudden Cardiac Death in Hemodialysis Patients: an In-Depth Review , Am J Kidney Dis 57(6)921:929.
[NPL] Rajan et al. Generalized Feature Extraction for Time-Varying Autoregressive Models, IEEE Transacion Signal Processing vol. 44, No. 10.
Castellanos, et al, Clinical Relevance of Intraperitoneal Pressure in Peritoneal Dialysis Patients, Perit Dial Int. Sep.-Oct. 2017;37(5):562-567. doi: 10.3747/pdi.2016.00267. Epub Jul. 11, 2017.
Chinese OA in 201710669452.2 of Oct. 16, 2019.
Chinese Office Action for App. No. 201710669451.8, dated Sep. 12, 2019.
Chinese Office Action for App. No. 201710669452.2, dated Dec. 3, 2019.
Chinese Office Action for App. No. 2019071601874110, dated Jul. 19, 2019.
Chinese Office Action in App. No. 201480059332.5, dated Mar. 30, 2018.
European Search Report for App. No. 17185636.2, dated Mar. 27, 2018.
European Search Report for App. No. 14859115.9, dated Jan. 5, 2018.
European Search Report for App. No. 17185636.2 dated Jan. 10, 2018.
European Search Report for App. No. 17185638.8, dated Dec. 19, 2017.
European Search Report for App. No. 17185808.7, dated Jan. 2, 2018.
European Search Report for App. No. 17185810.3, dated Dec. 15, 2017.
European Search Report for App. No. 17190053.3, dated Jan. 2, 2018.
European Search Report for App. No. 17190066, dated Jan. 16, 2018.
European Search Report for App. No. 17190084, dated Feb. 9, 2018.
Henderson, et al, "Online Preparation of Sterile Pyrogen-Free Electrolyte Solution," Trans. Am. Soc. Artif.Intern.Organs, 1978 pp. 465-467.
Indian OA of Nov. 21, 2019 in 2981/KOLNP/2013.
International Preliminary Report on Patentability for App. No. PCT/US2019/019334, dated Jun. 12, 2019.
Laurent, Jeanpierre, "Continuous Monitoring of Dynamic Systems: Application to Monitoring of Dialyzed Patients" Oct. 30, 2004, received from internet: http://laurent.jeanpierre1.free.fr/recherche/papiers/aista2004.pdf.
Office Action in Chinese App. No. 201710778666.3 dated Sep. 19, 2019.
PCT/US2016/058579 International Search Report dated Jan. 31, 2017.
PCT/US2016/058579_WO.
PCT/US2017/025868 International Search Report dated Jun. 29, 2017.
PCT/US2017/025868 Written Opinion dated Jun. 29, 2017.
PCT/US2017/030377_ISR.
PCT/US2017/030377_WO.
PCTUS20170146199 ISR and written opinion, dated Feb. 19, 2018.
PCTUS2017025858 International Search Report dated Jun. 29, 2017.
PCTUS2017025858 Written Opinion dated Jun. 29, 2017.
PCTUS2017025876 International Search Report dated Jun. 29, 2017.
PCTUS2017025876 Written Opinion dated Jun. 29, 2017.
Wollenstein, et al, "Colorimetric gas sensors for the detection of ammonia, nitrogen dioxide, and carbon monoxide: current status and research trends", Sensor and Test Conference 2011, Jan. 2, 2011, pp. 562-567.
Written Opinion in Dutch App. No. 2018577, dated Nov. 2, 2017.

\* cited by examiner

PERITONEAL DIALYSIS ADEQUACY MEAUREMENTS

CROSS-REFERENCE TO RELATED APPLICATION

This application claims the benefit of and priority to U.S. Provisional Patent Application No. 62/768,320 filed Nov. 16, 2018, the entire disclosure of which is incorporated by reference herein.

FIELD OF THE INVENTION

The invention relates to devices, systems, and methods for measuring dialysis adequacy in patients undergoing Peritoneal Dialysis (PD) treatment. The devices, systems, and methods use one or more flow sensors and one or more uremic solute sensors to measure the uremic solute concentration and volume of the peritoneal dialysate removed from the patient and to calculate the dialysis adequacy based on the measured peritoneal dialysate concentration and volume.

BACKGROUND

Peritoneal Dialysis (PD) is a dialysis treatment where a peritoneal dialysis fluid is cycled into and out of a peritoneal cavity to perform exchange across the peritoneum of the patient. Toxins and metabolic waste products are exchanged between the fluid injected into the peritoneum and the vascularized peritoneal membrane. To measure sufficiency of therapy, dialysis adequacy can be used as a performance metric. Dialysis adequacy is used to measure and to help ensure that patients are receiving a proper dose of dialysis therapy and to set a patient's peritoneal dialysis prescription. Known methods and systems commonly estimate dialysis adequacy by sending the removed fluid to a laboratory for analysis and either weighing an amount of the removed fluid or measuring the amount of fluid removed based on the time to drain the fluid and the flow rate. Alternatively, a blood urea concentration for the patient before and after treatment can be measured to determine the dialysis adequacy.

However, the known methods and systems fail to account for variation in determining dialysis adequacy. Due to the differences in performing PD and hemodialysis (HD), the corresponding clearance measurements can be different depending on the treatment modality. For example, in PD small solute clearance is usually measured by urea clearance normalized to total body water (Kt/V) or creatinine clearance normalized to body surface area, and includes a dialytic and a residual renal component. The residual renal component can be important in PD because the component can account for a significant proportion of the overall clearance achieved. In contrast, the residual renal component is oftentimes not considered in HD. Further, many PD patients have a more active and variable lifestyle, which may make standard assessments of urea clearance by blood draws and analysis more inconvenient. Known systems and methods do not account for these variations in clearances for a patient. Notably, the dialytic component is the only component that can be directly modified via a prescribing physician.

The known methods and systems also cannot provide a real-time or nearly-real time assessment of dialysis adequacy for peritoneal dialysis, nor can the known systems provide assessment of peritoneal membrane transport and/or ultrafiltration capability. If a patient undergoes HD, any residual kidney function quickly diminishes, but with PD residual kidney function can persist, making residual kidney function an important part of Kt/V measurements in PD. Moreover, the known systems and methods adjust patient prescription based on infrequently collected labs, typically once a month or less. As a result, changes in PD efficacy that occur between collections go undetected and untreated, leading to reduced overall effectiveness of dialysis. To measure Kt/V, known methods and systems require aliquots of spent peritoneal dialysate to be removed from a patient and then weighed to determine the total volume removed. For patients that have significant residual kidney function, such as patients producing >100 ml/day of urine, the urine must also be tested. The existing methods and systems require that the aliquot of the spent peritoneal dialysate be then physically transferred to a laboratory and then analyzed to determine the urea concentration. The process takes considerable time and is only performed periodically. The process is burdensome to the patient, because the patient needs to transport their waste PD fluid and urine to a clinic. The process is also costly to run. The known methods and systems also fail to take into account substantial natural intra-individual variation between clearance measurements, even if repeated clearance measurements are performed in the same patient for the same prescription. The variation is particularly marked for the residual renal component of clearance. Some of the variation may be accounted for by inaccuracies in collections of dialysate and urine, but other variations can result from day-to-day variation in urinary volume, peritoneal ultrafiltration, degree of equilibration, alterations in hydration, fluid intake, timing of exchanges, and tonicity of peritoneal fluids used. Therefore, periodic measurements of clearance as performed by the known systems and methods are not real-time, costly, and burdensome to the patient. Moreover, periodic measurements do not adequately characterize day to day variability for the patient. Because PD is generally performed at home instead of a dialysis clinic, there are fewer opportunities for the patient to interact with physicians or healthcare providers, resulting in fewer opportunities to test adequacy. Patient compliance to periodic testing may also be an issue with PD because patients do not come to a dialysis clinic as in hemodialysis (HD).

Hence, there is a need for systems and methods for measuring and calculating dialysis adequacy, and in particular Kt/V for peritoneal dialysis patients using sensors integrated into a PD system or method. The need includes calculating the dialysis adequacy in peritoneal dialysis in real-time or nearly real-time. The need further includes sensors positioned in the PD system to obtain measurements that can be used to determine dialysis adequacy. The need further includes sensors positioned in a catheter of a peritoneal dialysis system. The need includes a processor for determining dialysis adequacy based on sensor measurements. The need also includes avoiding human error in collecting samples, variations in day-to-day variation in urinary volume, peritoneal ultrafiltration, degree of equilibration, alterations in hydration, fluid intake, timing of exchanges, and tonicity of peritoneal fluids used. The need further includes automated systems and methods that do not require removing fluid samples, weighing the fluid samples, and physically sending the fluid samples for analysis to a laboratory. The need includes accounting for the residual renal component in determining dialysis adequacy. The need extends to systems and methods that can measure clearance and provide the dialysis adequacy of each peritoneal dialysis session or cycle. The need includes systems and methods for less expensive and burdensome clearance measurements to provide for more frequent measurements that better capture the patient's normal variability in clearance and to allow physicians to better manage the patient.

SUMMARY OF THE INVENTION

The first aspect of the invention relates to a system. In any embodiment, the system can comprise a catheter for removing peritoneal dialysate from a patient; a fluid line fluidly connected to the catheter, or a reservoir fluidly connected to the catheter; one or more flow sensors in any one or more of the catheter or the fluid line; one or more uremic solute sensors measuring a uremic solute concentration in a peritoneal dialysate removed from the patient; and a processor in communication with the one or more flow sensors and one or more uremic solute sensors, wherein the processor is programmed to calculate a clearance based on measurements obtained from the one or more flow sensors and one or more uremic solute sensors.

In any embodiment, the processor can be programmed to calculate a dialysis adequacy using an equation Kt/V; wherein K is equal to clearance, t is time, and V is a patient water volume.

In any embodiment, the system can comprise an osmotic agent sensor in the catheter, in the reservoir fluidly connected to the catheter, or in the fluid line fluidly connected to the catheter. In any embodiment, the osmotic agent sensor can be a glucose sensor.

In any embodiment, the processor can be programmed to estimate a peritoneal membrane transport capability for a patient based on an osmotic agent concentration in a peritoneal dialysate at three or more time points during a peritoneal dialysis cycle. In any embodiment, the osmotic agent concentration can be a glucose concentration.

In any embodiment, the processor can be programmed to calculate a total Kt/V for the patient using an equation: total Kt/V is equal to Kt/V from dialysis and Kt/V from residual kidney function.

In any embodiment, the processor can be programmed to calculate the Kt/V from residual kidney function using an equation: Kt/V from residual kidney function=$U/P \times L_u/V$, wherein U is a uremic solute concentration in urine of the patient, P is a blood uremic solute concentration, and $L_u$ is a volume of urine produced.

In any embodiment, the processor can be programmed to receive the uremic solute concentration in urine and volume of urine produced from the patient.

In any embodiment, the processor can be programmed to estimate the patient water volume based on a patient weight.

In any embodiment, the one or more uremic solute sensors can be positioned in the catheter.

In any embodiment, the one or more uremic solute sensors can be positioned in a fluid line or reservoir fluidly connected to the catheter.

In any embodiment, the processor can calculate a clearance based on measurements obtained from the one or more flow sensors and one or more uremic solute sensors in real-time or nearly real-time.

In any embodiment, the uremic solute can be selected from the group consisting of urea, creatinine, beta-2 microglobulin, uric acid, and combinations thereof.

In any embodiment, the uremic solute sensors can be selected from the group consisting of a urea sensor, a creatinine sensor, a beta-2 microglobulin sensor, a uric acid sensor, and combinations thereof.

The features disclosed as being part of the first aspect of the invention can be in the first aspect of the invention, either alone or in combination, or follow a preferred arrangement of one or more of the described elements.

The second aspect of the invention is drawn to a method. In any embodiment, the method can comprise the steps of: calculating a clearance based on a uremic solute concentration in a peritoneal dialysate removed from a patient measured by one or more uremic solute sensors and a volume of peritoneal dialysate removed from a patient measured by one or more flow sensors.

In any embodiment, the method can comprise the step of calculating a dialysis adequacy using an equation Kt/V; wherein K is equal to clearance, t is time, and V is a patient water volume.

In any embodiment, the urea clearance can be calculated by an equation clearance=$F/P \times L$, wherein F is the uremic solute concentration in the peritoneal dialysate removed from a patient, P is a blood uremic solute concentration of the patient, and L is the volume of peritoneal dialysate removed from the patient.

In any embodiment, the uremic solute concentration in the peritoneal dialysate can be measured with a uremic solute sensor in a catheter, a fluid line fluidly connectable to the catheter, or a reservoir fluidly connectable to the catheter.

In any embodiment, the volume of peritoneal dialysate removed from the patient can be measured with a flow sensor in a catheter, a fluid line fluidly connectable to the catheter, or a reservoir fluidly connectable to the catheter.

In any embodiment, P can be calculated using an equation P=$F/(T \times D)$, wherein T is a time point during a peritoneal dialysis cycle and D is a diffusion coefficient for a patient.

In any embodiment, the uremic solute concentration of the peritoneal dialysate can be measured at an end of a peritoneal dialysis cycle, and P can be calculated using an equation P=total uremic solute/V; wherein the total uremic solute is calculated using an equation total uremic solute=$F*L+F*(V-UF)$, wherein UF is an ultrafiltration volume for the peritoneal dialysis cycle.

In any embodiment, the method can comprise the step of calculating a Kt/V from residual kidney function.

In any embodiment, the Kt/V from residual kidney function can be calculated using an equation Kt/V from residual kidney function=$U/P \times L_u/V$, wherein U is a uremic solute concentration in urine of the patient and $L_u$ is a volume of urine produced.

In any embodiment, the method can comprise the step of calculating a total Kt/V for the patient using an equation total Kt/V is equal to Kt/V from dialysis and Kt/V from residual kidney function.

In any embodiment, the method can comprise the step of estimating a peritoneal membrane transport capability for the patient using an osmotic agent sensor in the catheter, a fluid line fluidly connectable to the catheter, or a reservoir fluidly connectable to the catheter. In any embodiment, the osmotic agent sensor can be a glucose sensor.

In any embodiment, the step of determining dialysis adequacy from dialysis can be performed by a processor of a peritoneal dialysis system.

In any embodiment, the uremic solute can be selected from the group consisting of urea, creatinine, beta-2 microglobulin, uric acid, and combinations thereof.

The features disclosed as being part of the second aspect of the invention can be in the second aspect of the invention, either alone or in combination, or follow a preferred arrangement of one or more of the described elements.

DETAILED DESCRIPTION OF THE INVENTION

Figure 1:
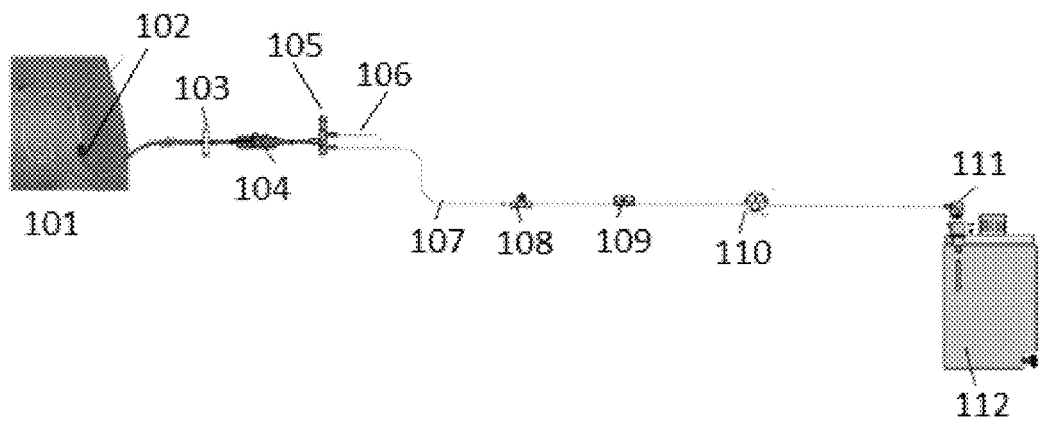
FIG. 1 illustrates a peritoneal dialysis cycler for calculating the dialysis adequacy for a patient.

Unless defined otherwise, all technical and scientific terms used have the same meaning as commonly understood by one of ordinary skill in the art.

The articles "a" and "an" are used to refer to one or to over one (i.e., to at least one) of the grammatical object of the article. For example, "an element" means one element or over one element.

The phrase "based on" generally means using one or more inputs to add, delete, update, or change in any way another one or more, or same, variable or parameter due to, or because of, the one or more inputs.

"Beta-2 microglobulin" is a protein making up one chain of the major histocompatibility complex. As used herein, "beta-2 microglobulin" can refer to the protein in solution, or in any state of matter.

A "beta-2 microglobulin sensor" is a component capable of measuring a concentration of beta-2 microglobulin in a fluid, a gas, or combinations thereof. Such components of measuring beta-2 microglobulin concentration can be by direct methods quantifying the actual presence of beta-2 microglobulin, or indirectly by measuring the byproducts of beta-2 microglobulin, or by subsequent reaction with beta-2 microglobulin or beta-2 microglobulin's by products.

The term "blood uremic solute concentration" refers to the concentration of a uremic solute in the blood of a patient.

The terms "calculating" or to "calculate" refer to obtaining a value for a parameter using one or more mathematical equations.

A "catheter" is a single or plural lumen tube for flowing a fluid, gas, combinations of substances, solutes, and any combination thereof from a first location to another. For example, a catheter can introduce or remove fluid to a body cavity of a patient.

In general, the term "clearance" refers to an amount of a given substance removed from a patient. The fluid can be the blood of a patient during dialysis. In certain embodiments, clearance can be the amount of the substance removed from the patient as a fraction of the total amount of the substance in the patient.

The terms "communication" or "electronic communication" can refer to the ability to transmit electronic data, instructions, information wirelessly, via electrical connection, or any other electrical transmission between two components or systems.

The term "comprising" includes, but is not limited to, whatever follows the word "comprising." Use of the term indicates the listed elements are required or mandatory but that other elements are optional and may be present.

The term "consisting of" includes and is limited to whatever follows the phrase "consisting of" The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

"Creatinine" refers to $C_4H_7N_3O$ in solution, liquid, gaseous, or solid form.

A "creatinine sensor" is a component capable of measuring a concentration of creatinine in a fluid, a gas, or combinations thereof. Such components of measuring creatinine concentration can be by direct methods quantifying the actual presence of creatinine, or indirectly by measuring the byproducts of creatinine, or by subsequent reaction with creatinine or creatinine's by products.

The terms "determining," "determines," and the like, generally refer to, in the broadest reasonable interpretation, any process or method for obtaining or coming to a decision, value, number, or finding, for any one or more value, output, parameter, or variable, by any means applicable to the relevant parameter being determined.

The term "dialysis adequacy" refers to an amount, or dosage, of treatment by dialysis. Dialysis adequacy can refer to a measurement of the amount of solutes cleaned from the blood of a patient by dialysis therapy.

The term "diffusion coefficient" refers to the rate at which solutes pass through a membrane of a patient. The diffusion coefficient can be for a specific type of membrane, such as the peritoneum.

An "end of a peritoneal dialysis cycle" refers to a time point during peritoneal dialysis cycle during or just prior to draining the peritoneal dialysate from the patient.

"Estimated," "estimating," to "estimate," or "estimation" can each refer to a determination of one or more parameters indirectly using one or more variables.

The term "flow sensor" refers to any component capable of measuring a volume or a rate of fluid moving through from a first point to a second point.

The term "fluidly connectable" refers to a capability for providing the passage of fluid, gas, or combination thereof, from one point to another point. The ability of providing such passage can be any connection, fastening, or forming between two points to permit the flow of fluid, gas, or combinations thereof. The two points can be within or between any one or more of compartments of any type, modules, systems, components, and rechargers.

The term "fluidly connected" refers to a particular state such that the passage of fluid, gas, or combination thereof, is provided from one point to another point. The connection state can also include an unconnected state, such that the two points are disconnected from each other to discontinue flow. It will be further understood that the two "fluidly connectable" points, as defined above, can from a "fluidly connected" state. The two points can be within or between any one or more of compartments, modules, systems, components, and rechargers, all of any type.

A "fluid line" can be any conduit or passageway that permits flow of a liquid, gas, or combination thereof from a first point to a second point.

The term "glucose concentration" refers to an amount of glucose dissolved in a given volume of solvent.

A "glucose sensor" is a component capable of measuring a concentration of glucose in a fluid.

"Kt/V from dialysis" is a measurement of dialysis adequacy based on dialysis treatment. In general, Kt/V is a ratio of the volume of fluid cleared of a solute divided by the distribution volume of the solute in a patient where the factor Kt represents the volume of fluid expected to be cleared of the solute during a specified period of time and V is a volume of distribution of the solute, approximately equal to patient's total body water, a volume of water in a patient prior to starting dialysis, for which Kt/V is measured. In particular, K can represent clearance of the solute or the volume of blood that is completely cleared of the solute as a function of time, and is oftentimes expressed in milliliters per minute (mL/min), and t represents time.

"Kt/V from residual kidney function" is a measurement of a solute removed from a patient by action of the patient's kidneys. The solutes removed by residual kidney function is generally removed in urine.

The term "measurement," "measuring," or to "measure" refers to determining a state or parameter of a system or substance. For example, a sensor can obtain measurements of a uremic solute.

An "osmotic agent" is a substance dissolved in water capable of driving a net movement of water by osmosis across a semi-permeable membrane due to concentration differences of the osmotic agent on each side of the semi-permeable membrane. Osmotic agents can include glucose, icodextrin, dextrose, and any other suitable substance or compound known to those of skill in the art for use as an osmotic agent in peritoneal dialysis.

The term "osmotic agent concentration" refers to the amount of one or more osmotic agents in a fluid per unit volume.

A "patient" or "subject" can be a member of any animal species, preferably a mammalian species, optionally a human. The subject can be an apparently healthy individual, an individual suffering from a disease, or an individual being treated for a disease. In certain embodiments, the patient can be a human, sheep, goat, dog, cat, mouse or any other animal.

The term "patient water volume" refers to the total amount of water within a body of a patient.

The term "patient weight" refers to the mass of a patient. The patient weight can either refer to an ideal mass of the patient, or the actual mass of the patient including any additional fluid in the body of the patient.

"Peritoneal dialysate" is a fluid solution to be used in peritoneal dialysis having specified parameters for purity and sterility and containing one or more solutes. Peritoneal dialysate is different than the dialysate used in hemodialysis.

"Peritoneal dialysis" is a therapy wherein a peritoneal dialysate fluid infused into the peritoneal cavity, which serves as a natural dialyzer. In general, waste components diffuse from a patient's bloodstream across a peritoneal membrane into the dialysis solution via a concentration gradient and through the fluid that is transferred to the peritoneum. In general, excess fluid in the form of plasma water flows from a patient's bloodstream across a peritoneal membrane into the dialysis solution via an osmotic gradient. Once the infused peritoneal dialysis solution has captured sufficient amounts of the waste components the fluid is removed. The cycle can be repeated for several cycles each day or as needed.

The term "peritoneal dialysis cycle" or "cycle" refers to the infusion of peritoneal dialysate into a patient, a dwell of the peritoneal dialysate within the peritoneal cavity of the patient, and the removal of the peritoneal dialysate from the peritoneal cavity of the patient. The process of filling and then draining your abdomen can also be seen as an "exchange" of used and clean fluids. However, the number, length, and timing of "cycles" or "exchanges" are non-limiting. For example, Continuous Ambulatory Peritoneal Dialysis (CAPD), Assisted Peritoneal Dialysis (APD) and Continuous Cycling Peritoneal Dialysis (CCPD) may occur on different schedules, but the process of filling and then draining the peritoneal cavity can be referred to as "cycles" for CAPD, APD, and CCPD. As such, the term is "cycle" or exchange refers to any particular dialysis schedule or type of dialysis.

A "peritoneal dialysis system" is a set of components for conducting peritoneal dialysis therapy. The peritoneal dialysis system can include components for introducing peritoneal dialysate into a patient, draining peritoneal dialysate from a patient, and optionally generating peritoneal dialysate.

The term "peritoneal membrane transport capability" refers to the ability of solutes to pass through the peritoneal membrane.

The term "positioned" refers to a component connected to or in contact with the feature being referred to. The contact can be physical, fluid, or electrical and is intended to be used in the broadest reasonable interpretation.

The term "processor" as used is a broad term and is to be given its ordinary and customary meaning to a person of ordinary skill in the art. The term refers without limitation to a computer system, state machine, processor, or the like designed to perform arithmetic or logic operations using logic circuitry that responds to and processes the basic instructions that drive a computer. In any embodiment of the first, second, third, and fourth invention, the terms can include ROM ("read-only memory") and/or RAM ("random-access memory") associated therewith.

The term "programmed," when referring to a processor, can mean a series of instructions that cause a processor to perform certain steps.

The term "real-time" refers to decisions, determinations, or adjustments that are made concerning events that are ongoing as information is received or immediately after information is received. The terms "near real-time" or "nearly real-time" refers to decisions, determinations, or adjustments that can be made shortly after information is received.

The term "receiving" or to "receive" means to obtain information from any source.

The terms "removing" or to "remove" refer to withdrawing a substance from a container, conduit, or patient.

The term "residual kidney function" refers to the remaining ability of a patient's kidneys remove toxins and regulate solute and fluid levels in patients with kidney disease.

A "reservoir" can be a container or component that holds a liquid, fluid, gas, or combination thereof.

The term "sensor," as used herein, can be a converter of any type that can measure a physical property or quantity of a matter in a solution, liquid or gas, and can convert the measurement into a signal which can be read by an electronic instrument.

A "time point during a peritoneal dialysis cycle" refers to a length of time from a beginning of a peritoneal dialysate cycle to a specific moment afterwards.

"Total Kt/V" refers to a sum of the Kt/V resulting from dialysis of any type and the Kt/V from residual kidney function for a patient, such as residual renal function from micturition.

The term "total uremic solute" refers to the sum of the amount of a uremic solute in the blood of a patient and the amount of the uremic solute in peritoneal dialysate inside or removed from the patient.

The term "ultrafiltration volume" refers to a volume of water removed from the blood of a patient during dialysis treatment.

The term "uremic solute clearance" refers to an amount of a uremic solute removed from the blood of a patient. For example, a peritoneal urea clearance can be calculated by determining a urea concentration in a removed peritoneal dialysate divided by a total blood urea concentration multiplied by the total peritoneal dialysate volume. However, the uremic solute clearance can be based on any uremic solute, and need not involve urea.

The term "uremic solute concentration" refers to an amount of a uremic solute dissolved in a given volume of solvent.

"Urea" refers to CO(NH2)2 in solution, liquid, gaseous, or solid form.

A "urea sensor" is a component capable of measuring a concentration of urea in a fluid, a gas, or combinations thereof. Such components of measuring urea concentration can be by direct methods quantifying the actual presence of urea, or indirectly by measuring the by products of urea, carbon dioxide and ammonia in any physical state, or by subsequent reaction with urea or urea's by products.

A "uremic solute" is a nitrogenous substance dissolved in a solvent. Non-limiting examples of uremic solutes can include urea, creatinine, beta-2 microglobulin, uric acid, and others.

A "uremic solute sensor" is a component capable of measuring a concentration of a specified uremic solute in a fluid, gas, or combination thereof. The component can measure the uremic solute concentration by direct methods quantifying the actual presence of the uremic solute, or indirectly by measuring the by-products of the uremic solute in any physical state, or by subsequent reaction with the uremic solute or the uremic solute's by-products. One non-limiting group of uremic solute sensors can be selected from the group of a urea sensor, a creatinine sensor, a beta-2 microglobulin sensor, and a uric acid sensor.

"Uric acid" refers to C5H4N4O3 in solution, liquid, gaseous, or solid form.

A "uric acid sensor" is a component capable of measuring a concentration of uric acid in a fluid, a gas, or combinations thereof. Such components of uric acid concentration can be by direct methods quantifying the actual presence of uric acid, or indirectly by measuring the byproducts of uric acid, or by subsequent reaction with uric acid or uric acid's by products.

The term "urine" refers to a fluid containing waste solutes removed from the body by the kidneys.

The term "urine produced" refers to a fluid generated by the kidneys containing solutes from the body.

The term "volume" refers to the three-dimensional space occupied by a substance or container.

Dialysis Adequacy Measurements

The invention is drawn to systems and methods for determining the adequacy or Kt/V of treatment for patients undergoing peritoneal dialysis. FIG. 1 illustrates a peritoneal dialysis system that can be used to determine the Kt/V from dialysis for peritoneal dialysis patients. Peritoneal dialysate from a peritoneal dialysate source (not shown) can be introduced into the peritoneal cavity of a patient 101 through fluid line 106. The peritoneal dialysate passes valve 105 and connector 104 into catheter 102 for infusion into the patient 101. Optionally, a filter 103 can be included to remove any particulate matter prior to infusion into the patient 101. After a dwell period, the fluid in the peritoneal cavity is removed from the patient 101 through catheter 102 into fluid line 107. Valve 105 controls the movement of fluid during fill and drain cycles. Pump 110 provides the driving force necessary for removing the peritoneal dialysate from the patient 101. In certain embodiments, the fluid line 107 can be fluidly connected to a reservoir 112 through connector 111. Alternatively, the fluid line 107 can be connected to a drain for disposal of the used peritoneal dialysate.

The peritoneal dialysis system can include one or more sensors for measuring parameters that can be used to determine Kt/V from dialysis. As illustrated in FIG. 1, the sensors can include a flow sensor 108 and a uremic solute sensor 109. In certain embodiments, the uremic solute sensor 109 can be a urea sensor. Although urea is the most commonly used marker for measuring dialysis adequacy, any other uremic toxin such as creatinine, beta-2 microglobulin, or uric acid can be monitored including monitoring combinations of any one or more of the described markers. The uremic solute sensor can measure any known uremic solute concentration in the peritoneal dialysis fluid using any appropriate sensor known to those of ordinary skill in the art. For example, the uremic solute sensor 109 can be a creatinine sensor, a beta-2 microglobulin sensor, a uric acid sensor, or a sensor for any other known uremic toxin. In addition to being a urea sensor, the uremic solute sensor 109 can be any one of a creatinine sensor, a beta-2 microglobulin sensor, a uric acid sensor, or a sensor for any other known uremic toxin. The creatinine sensor can be accomplished by any number of electrochemical methods known to those of skill in the art. For example, a creatinine sensor can include a sensing element having a creatinine deiminase enzyme or a pH-indicating compound. The creatine sensor can have an electrode and/or an optical excitation assembly for illuminating the sensing element and/or an optical detection assembly to measure a parameter indicative of creatinine concentration. Measurement of beta-2-microglobulin can be accomplished with sensors having a sensing surface containing antibeta-2-microglobulin antibodies. Any other known beta-2-microglobulin sensors can be used. An example of a uric acid sensor can be a sensor having an enzyme uricase deposited on a substrate to measure uric acid. Other known uric acid sensors can be used. Optionally, additional sensors such as pressure sensors, glucose sensors, potassium sensors, calcium sensors, sodium sensors, magnesium sensors, conductivity sensors, or combinations thereof can be used to aid in the Kt/V calculations.

Although illustrated in FIG. 1 as positioned in fluid line 107, the uremic solute sensor 109 and flow sensor 108 can alternatively be positioned in the catheter 102, or in the reservoir 112 fluidly connectable to the catheter 102. The flow sensor 108 can be used to determine the volume of peritoneal dialysate removed from the patient 101 and can be avoided if the volume can be accurately measured inside reservoir 112. The uremic solute sensor 109 measures the dialysate uremic solute concentration for use in the Kt/V calculations. The sensors can be in communication with a processor (not shown) programmed to calculate the Kt/V from peritoneal dialysis. The processor can be part of the peritoneal dialysis system, or a separate component in communication with the sensors through wired or wireless communication.

Kt/V from peritoneal dialysis can comprise a peritoneal and a residual renal component. The residual renal component can be important in peritoneal dialysis because residual renal function can possibly account for a proportion of total clearance, depending on the patient and the duration of the first instance of treatment. As such, total Kt/V is equal to the sum of the peritoneal Kt/V and renal Kt/V. Typically, peritoneal Kt/V can be the 24-hour dialysate uremic solute nitrogen content/serum uremic solute nitrogen. Renal Kt/V can equal the 24-hour urine uremic solute nitrogen content/serum uremic solute nitrogen.

Kt/V is equal to the uremic solute clearance over the patient water volume. The patient water volume V can be estimated using the Watson formula, or 0.58×the ideal body weight of the patient, or alternatively estimated using any other formula, including patient height, patient weight, and/or gender. For example, the value V can be estimated using anthropometric formulas, including either Watson or Hume, based on age, sex, height, and weight. Estimates of V from the Watson formulas, when compared to a gold standard, such as deuterium oxide dilution, are, on average, slightly low but the discrepancy can vary substantially from patient to patient, especially in the obese. To determine the Kt/V from dialysis, the uremic solute clearance is required. EQ(1) provides a uremic solute clearance calculation using data from the flow sensor 108 and uremic solute sensor 109.

$$\text{Uremic solute clearance}_{dialysis} = F/P \times L \quad \text{EQ(1)}$$

Where F is the uremic solute concentration in the peritoneal dialysate removed from the patient, P is a blood uremic solute concentration of the patient, and L is the volume of peritoneal dialysate removed from the patient. The uremic solute concentration in the peritoneal dialysate removed from the patient can be measured by uremic solute sensor 109. The volume of peritoneal dialysate removed from the patient can be measured by flow sensor 108. The blood uremic solute concentration of the patient can be calculated or estimated. In certain embodiments, the blood uremic solute concentration can be measured by measuring the concentration of uremic solute in the dialysate as a function of time $d\varphi/dt$ and using Fick's Law, given in EQ(2).

$$\frac{\partial \varphi}{\partial t} = D\Delta\varphi \quad \text{EQ(2)}$$

Using Fick's Law, the patient blood uremic solute concentration can be modeled and estimated. The diffusion coefficient (D) can be patient and time dependent. D can be measured for a given patient using Peritoneal Equilibration Test (PET). The PET test characterizes the transport properties of a patient's peritoneum, by measuring the clearance rate of urea, creatinine, glucose and protein. The peritoneal equilibration test (PET) is an assessment of peritoneal membrane transport function in patients wherein solute transport rates are assessed by the rates of the solute's equilibration between the peritoneal capillary blood and dialysate. The ratio of solute concentrations in dialysate and plasma (D/P ratio) at specific times during a dwell can signify the extent of solute equilibration wherein D represents the concentration of the solute in the dialysate and P represents the concentration of the solute in the plasma. The ratio D/P can be determined for any solute that is transported from the capillary blood to the dialysate and represents the fraction of the solute that is cleared across the peritoneal membrane. Creatinine, urea, electrolytes such as magnesium, potassium, and calcium, phosphate, and proteins are commonly tested solutes for clinical use.

The PET test is generally conducted at initiation of peritoneal dialysis to establish the type of membrane for a particular patient and to guide the physician in setting the patient's prescription based on the assessment. In certain embodiments, the PET test can be conducted regularly to take into account any changes in the diffusion coefficient for a patient over time. However, the PET test requires a blood test to determine the blood concentrations of each of the solutes. Alternatively, the changes in the diffusion coefficient can be monitored using a modified PET test, which measures glucose transport as a function of time. As described, the peritoneal dialysis system can optionally include an osmotic agent sensor such as a glucose sensor, allowing for use of the modified PET test and calculation of the diffusion coefficient D. Based on the diffusion coefficient for glucose transport, the system can estimate the peritoneal membrane transport capability. The estimated peritoneal membrane transport capability can be based on information of the relative changes in the ability of uremic solutes to cross the peritoneal membrane compared to past measurements as evidenced by the diffusion coefficient for glucose. Based on the peritoneal membrane transport capability obtained from the dialysate-to-plasma ratio of any uremic solute such as creatinine and the dialysate glucose concentration at the end of the test compared to the start, a real-time or nearly real-time assessment of a patient's peritoneal membrane transport and ultrafiltration capability can be provided that is more precise than the typical categories of low (L), low-average (L-A), high-average (H-A), and high (H) transporters.

In certain embodiments, the dialysate glucose concentration can be measured at preset intervals at specified time points during a peritoneal dialysis cycle. A small amount of peritoneal dialysate can be removed from the patient at each time point, and the concentration of an osmotic agent determined with an osmotic agent sensor such as a glucose sensor. The preset intervals can be every 30 minutes, every hour, every two hours, or any other interval of time. In certain embodiments, at least three time points can be used for the modified PET test. The ratio of the osmotic agent concentration such as the glucose concentration at time T to the glucose concentration initially in the peritoneal dialysate can be used to estimate the diffusion coefficient D, and thereby estimate the peritoneal membrane transport capability. In certain patients with blood glucose levels greater than 235 mg/dL transport can be slowed because the gradient between the peritoneal dialysate and the blood is lower. A correction factor can be developed for diabetic patients with poor glucose control to allow use of the modified PET test.

As described, an osmotic agent sensor such as a glucose sensor can be positioned in a catheter, in a reservoir fluidly connected to the catheter, or in a fluid line fluidly connected to the catheter. Any sensor capable of determining the osmotic agent concentration can be used. In certain embodiments, the osmotic agent sensor could be of the type used for diabetes control. At pre-set intervals, an aliquot of PD fluid can be withdrawn from the patient's peritoneum, and the osmotic agent concentration such as the glucose concentration measured to give a time-dependent concentration gradient for osmotic agent. The gradient can be a function of osmotic agent absorption across the peritoneal membrane and dilution from ultrafiltration. At the end of the dwell period, the total fluid volume can be measured to determine the ultrafiltration component, which could be mathematically subtracted to give a total glucose flux into the patient. Knowing the osmotic agent concentration gradient between blood and peritoneal fluid, the osmotic agent flux into the patient can be used to determine the diffusion coefficient D used in the Fick's diffusion equation.

With a known diffusion coefficient, the blood uremic solute concentration of a patient can be estimated. In certain embodiments, the uremic solute concentration of the peritoneal dialysate can be measured soon after the peritoneal dialysate has been introduced into the patient. In such cases, the patient blood uremic solute concentration can be given by EQ(3), where T is the time point during a peritoneal dialysis cycle.

$$P = F/(T \times D) \qquad \text{EQ(3)}$$

Alternatively, the dialysate uremic solute concentration can be measured at the end of a peritoneal dialysis cycle, under assumption that F and P have equilibrated. In such cases, the uremic solute clearance can be calculated using EQ (4)

$$\text{Uremic solute clearance} = F \times \text{dialysate volume (Infused+UF)} \qquad \text{EQ(4)}$$

Where UF is an ultrafiltration volume for a peritoneal dialysis cycle. The patient blood uremic solute concentration is given by EQ(5)

$$\text{Uremic solute patient} = F \times (V - UF) \qquad \text{EQ(5)}$$

because the blood uremic solute concentration is assumed to be equilibrated with the dialysate uremic solute concentration. The total uremic solute is the sum of the patient blood uremic solute concentration and the uremic solute clearance. The patient pre-dialysis blood uremic solute concentration can be found with EQ(6)

$$\text{Total uremic solute}/V = \text{pre-dialysis blood level} \qquad \text{EQ(6)}$$

With a known patient pre-dialysis blood uremic solute level, the Kt/V from dialysis can be calculated as described. The processor of the invention can automatically calculate the Kt/V in real-time or nearly real-time. The systems and methods can calculate the Kt/V as information from the sensors as data is received. For example, as flow rate and uremic solute concentration values are received by the processor, the processor can immediately determine the Kt/V for that session.

An aliquot of peritoneal dialysate can be removed from the patient during a first portion of a cycle after the uremic solute in the blood has equilibrated with the dialysate. For example, an aliquot can be removed after a set time period, such as 10 minutes, after filling the peritoneal cavity with dialysate. The initial equilibrated uremic solute concentration can be used to determine the initial patient blood uremic solute concentration. As described, the patient blood concentration at the end of a session can be determined from the dialysate uremic solute concentration at the end of the session. Using the pre and post-session patient blood uremic solute levels, the uremic solute reduction ratio can be obtained. From the uremic solute reduction ratio, clearance can be determined using EQ(7).

$$Kt/V \text{ from dialysis} = -\ln(1 - URR) \qquad \text{EQ(7)}$$

Certain peritoneal dialysis patients have some level of residual kidney function. In such patients, the total Kt/V is the sum of the Kt/V from dialysis and the Kt/V from urine production. In calculating the total Kt/V to determine dialysis adequacy, the contribution from urine production in patients with a higher degree of residual kidney function can be taken into account. In certain embodiments, the system can take into account the Kt/V contribution from urine production for patients with a predetermined level of urine production, such as 100 mL/day, while ignoring the Kt/V for patients with lower residual kidney function. The predetermined threshold can be set higher or lower than 100 mL/day of urine production, including between 10 mL/day and 200 mL/day, between 10 mL/day and 50 mL/day, between 25 mL/day and 75 mL/day, between 50 mL/day and 150 mL/day, between 75 mL/day and 125 mL/day, between 100 mL/day and 150 mL/day, or between 125 mL/day and 200 mL/day. In certain embodiments, the Kt/V from residual kidney function can be taken into account for patients with any volume of urine production greater than 0. The contribution from residual kidney function can be calculated using EQ(8).

$$Kt/V \text{ from residual kidney function} = U/P \times L_u/V \qquad \text{EQ(8)}$$

where U is the concentration of uremic solute in urine of the patient and $L_u$ is a total volume of urine produced. As described, the patient blood uremic solute concentration P and the patient water volume V can be estimated. As described herein, the processor of the invention can automatically calculate the Kt/V in real-time or nearly real-time. The systems and methods can calculate the Kt/V as information from the sensors as measurements are received.

The concentration of uremic solute in urine can be determined by any method known in the art. In certain embodiments, uremic solute sensors can be used to measure the urine concentration of uremic solute. Alternatively, test strips can be used. Test strips for measuring the uremic solute concentration in urine are commercially available. The patient can use a test strip to determine the concentration of uremic solute in the urine and the concentration can be received by the processor. The patient can manually input the concentration of uremic solute in urine to the processor using an interface. Alternatively, digital readings of the concentration of uremic solute in urine can be made and communicated to the processor through wired or wireless communication. In certain embodiments, the concentration of uremic solute in urine can be modeled or estimated based on historical measurements for the patient. The volume of urine produced $L_u$ can be measured by the patient and received by the processor.

In certain embodiments, the uremic solute sensors of the dialysis system can be used to measure the uremic solute concentration in the urine. A sample of the patient's urine can be introduced to a flow path having a uremic solute sensor, such as the flow path illustrated in FIG. 1. In certain embodiments, the uremic solute concentration in the urine can be measured once, or at infrequent intervals. The measured uremic solute concentration in the urine can then be used as an estimate of the uremic solute concentration in the urine at later points in time, avoiding the need to measure the uremic solute concentration in the urine each time while improving the measurements.

Alternatively, the Kt/V from residual kidney function can be provided as a quantitative index. For example, a large urine output can be given a value of 5, no input can be given a value of 0, and intermediate amounts of urine output can be given values of 1-4. One of skill in the art will understand that any values can be used in the quantitative index. Using a quantitative index simplifies ambulatory measurements so that the patient does not need to measure the amount of urine and the uremic solute concentration at home.

The total Kt/V for a patient can be determined by the processor using EQ(9).

$$\text{Total } Kt/V = Kt/V \text{ for dialysis} + Kt/V \text{ from urine} \qquad \text{EQ(9)}$$

Current guidelines suggest a weekly Kt/V of 1.7 or daily of 0.24 are recommended minimums. Based on the total Kt/V calculation, the patient or caregiver can make any necessary adjustments to the peritoneal dialysis prescription to ensure the total Kt/V meets the minimum recommendations.

Figure 2:
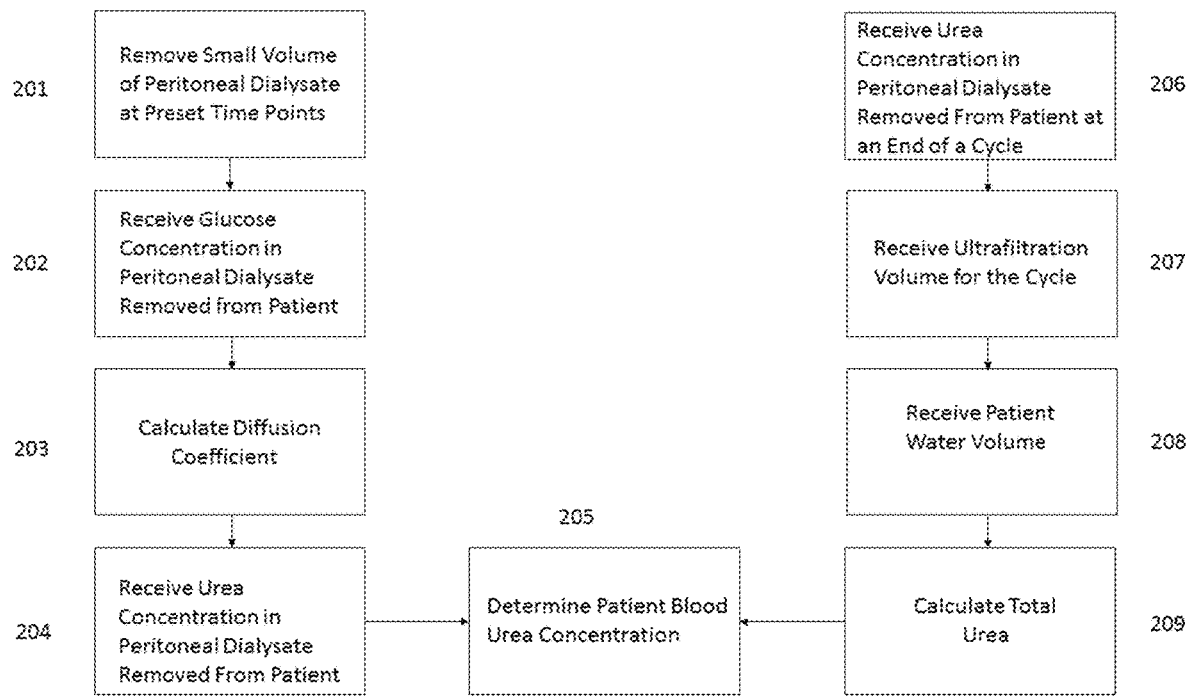
FIG. 2 is a flow chart illustrating a method of calculating a patient blood urea concentration.

FIG. 2 illustrates a flow chart for estimating a blood urea concentration of a patient. Although FIG. 2 illustrates the method for estimating a blood urea concentration, as described, the same method can be used for any uremic solute. In step 201, small amounts of peritoneal dialysate can be removed from the patient at preset time points during a peritoneal dialysis cycle. In step 202, the glucose concentration of the peritoneal dialysate removed from the patient at the preset time points can be received by the system using an osmotic agent sensor such as a glucose sensor in a catheter, a fluid line fluidly connected to the catheter, or reservoir fluidly connected to the catheter. Using the change in glucose concentration with respect to time, the diffusion coefficient for the patient can be calculated or estimated in step 203, and the peritoneal membrane transport capability estimated. The urea concentration in the peritoneal dialysate removed from the patient can be received in step 204 from a urea sensor in a catheter, a fluid line fluidly connected to the catheter, or a reservoir fluidly connected to the catheter. With a known or estimated diffusion coefficient and a known urea concentration in the peritoneal dialysate removed from the patient, the patient blood urea concentration can be determined in step 205 using EQ(3). One of skill in the art will understand that the order of steps 203 and 204 can be reversed, or that steps 203 and 204 can be performed simultaneously by a processor in the peritoneal dialysis system.

Alternatively, the urea concentration in the peritoneal dialysate removed from the patient at an end of a cycle can be received in step 206. An ultrafiltration volume for the cycle can be received by the system in step 207. The ultrafiltration volume for the cycle can be measured by subtracting a volume of peritoneal dialysate infused into the patient from the volume of peritoneal dialysate removed from the patient. The volumes infused into and removed from the patient can be measured with flow sensors in the catheter or fluid lines of the peritoneal dialysis system. In step 208, the patient water volume can be received. The patient water volume can be estimated using anthropometric formulas, including either Watson or Hume, based on age, sex, height, and weight. The total urea volume can be calculated in step 209 using EQ(6), if the blood and dialysate urea concentrations have equilibrated by an end of a cycle. Using the total urea concentration and the patient water volume, the initial patient blood urea concentration can be determined in step 205, as described. One of skill in the art will understand that steps 206-209 can be performed in any order or can be performed simultaneously by a processor in the peritoneal dialysis system.

The system can use either the method illustrated in steps 201-205 or the method illustrated in steps 206-210 to determine the patient blood urea concentration. In certain embodiments, the system can use both methods to determine the patient blood urea concentration with two independent methods. The system can use the values obtained from each method to check the accuracy or can average the values obtained from each method to obtain a more accurate blood urea concentration.

Figure 3:
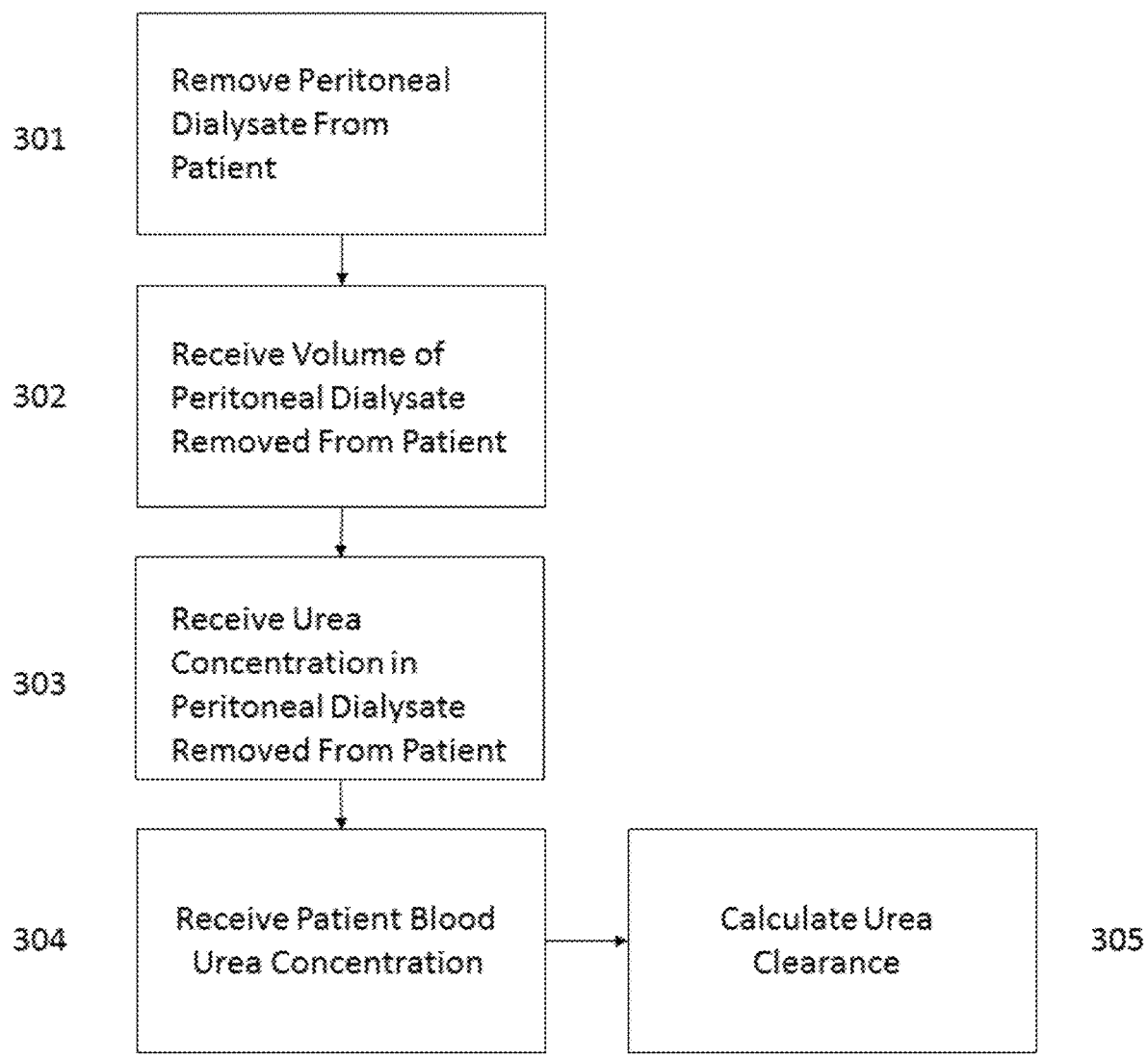
FIG. 3 is a flow chart illustrating a method of calculating urea clearance for a patient.

FIG. 3 illustrates a flow chart for calculating urea clearance using sensors in a peritoneal dialysis system. As described, any uremic solute can be used in calculating clearance using the same method. In step 301, peritoneal dialysate can be removed from a patient. In step 302, the volume of peritoneal dialysate removed from the patient can be received by a processor of the system. The volume of peritoneal dialysate removed from the patient can be measured by a flow sensor in a catheter or a fluid line fluidly connected to the catheter of a peritoneal dialysis system. In step 303, the urea concentration of the peritoneal dialysate removed from the patient can be received by the system. The urea concentration of the peritoneal dialysate removed from the patient can be measured by a urea sensor in a catheter, a fluid line fluidly connected to the catheter, or a reservoir fluidly connected to the catheter. In step 304, the blood urea concentration of the patient can be received by a processor of the system. As described, the blood urea concentration can be determined by analysis of the patient's blood, or by the method illustrated in FIG. 2. Using the blood urea concentration of the patient, the volume of peritoneal dialysate removed from the patient, and the urea concentration in the peritoneal dialysate removed from the patient, the urea clearance for the patient can be calculated in step 305 using EQ(1).

One of skill in the art will understand that steps 302-304 can be performed in any order or can be performed simultaneously. For example, the blood urea concentration of the patient in step 304 can be received prior to or simultaneously to the urea concentration or volume of the peritoneal dialysate removed from the patient.

Figure 4:
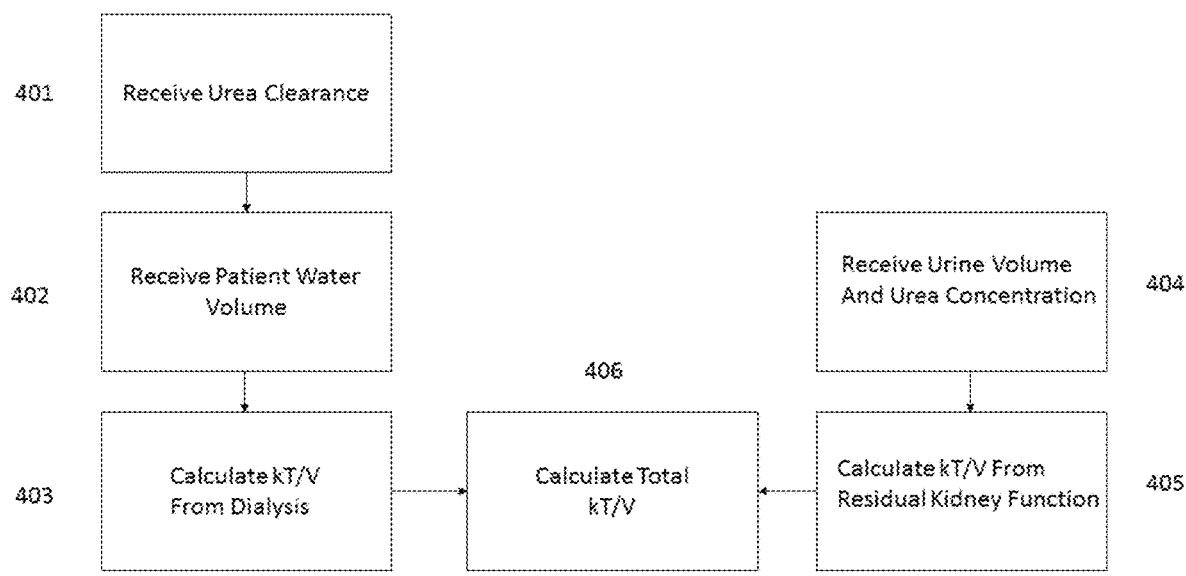
FIG. 4 is a flow chart illustrating a method of calculating Kt/V for a patient.

FIG. 4 illustrates a flow chart for calculating the total Kt/V for a patient. In step 401, the patient water volume can be received. In step 402, the urea clearance can be obtained. The urea clearance can be determined as illustrated in FIG. 3. In step 403, the Kt/V from dialysis can be calculated using the urea clearance over the patient water volume. Optionally, for patients with significant residual kidney function, the system can receive the total volume of urine produced by the patient and the urea concentration of the urine produced by the patient in step 404. In step 405, the Kt/V from residual kidney function can be calculated using EQ(8). In step 406, the system can determine the total Kt/V for the patient by from both dialysis and residual kidney function using EQ(9). Although FIG. 4 illustrates calculating a total Kt/V using urea concentrations, any uremic solute can be used, including creatinine, beta-2 microglobulin, uric acid, or any other known uremic toxin.

One skilled in the art will understand that various combinations and/or modifications and variations can be made in the described systems and methods depending upon the specific needs for operation. Moreover, features illustrated or described as being part of an aspect of the invention may be used in the aspect of the invention, either alone or in combination, or follow a preferred arrangement of one or more of the described elements.

We claim:

1. A system, comprising:
   a catheter (102) for removing peritoneal dialysate from a patient; a fluid line (107) fluidly connected to the catheter, or a reservoir (112) fluidly connected to the catheter;
   one or more flow sensors (108) in the catheter;
   one or more uremic solute sensors (109) measuring a uremic solute concentration in a peritoneal dialysate removed from the patient;
   at least one glucose sensor measuring a glucose concentration in the peritoneal dialysate removed from the patient; and
   a processor in communication with the one or more flow sensors and the one or more uremic solute sensors, wherein the processor is programmed to calculate a clearance based on measurements obtained from the one or more flow sensors and the one or more uremic solute sensors; the processor is programmed to cause removal of a portion of dialysate to be removed from the patient during a peritoneal dialysis dwell period;
   and the processor further programmed to calculate a diffusion coefficient during the peritoneal dialysis dwell period based on data received from the at least one glucose sensor during the same peritoneal dialysis dwell period.

2. The system of claim 1, wherein the processor is programmed to calculate a dialysis adequacy using an equation Kt/V; wherein K is equal to clearance, t is time, and V is a patient water volume.

3. The system of claim 1, the processor programmed to estimate a peritoneal membrane transport capability for the patient based on the data received from the at least one glucose sensor at three or more time points during a peritoneal dialysis cycle.

4. The system of claim 1, the processor programmed to calculate a total Kt/V for the patient using an equation: total Kt/V is equal to Kt/V from dialysis and Kt/V from residual kidney function.

5. The system of claim 4, the processor programmed to calculate the Kt/V from residual kidney function using an equation: Kt/V from residual kidney function=$U/P \times L_u/V$, wherein U is a uremic solute concentration in urine of the patient, P is a blood uremic solute concentration, and $L_u$ is a volume of urine produced.

6. The system of claim 5, the processor programmed to receive the uremic solute concentration in urine and volume of urine produced from the patient.

7. The system of claim 1, the processor programmed to estimate the patient water volume based on a patient weight.

8. The system of claim 1, wherein the one or more uremic solute sensors are positioned in the catheter.

9. The system of claim 1, wherein the one or more uremic solute sensors are positioned in a fluid line or reservoir fluidly connected to the catheter.

10. The system of claim 1, wherein the processor calculates a clearance based on measurements obtained from the one or more flow sensors and one or more uremic solute sensors in real-time or nearly real-time.

11. The system of claim 1, wherein the uremic solute is selected from the group consisting of urea, creatinine, beta-2 microglobulin, uric acid, and combinations thereof.

12. The system of claim 1, wherein the one or more uremic solute sensors is selected from the group consisting of a urea sensor, a creatinine sensor, a beta-2 microglobulin sensor, a uric acid sensor, and combinations thereof.

13. A method, comprising the steps of:
calculating a clearance based on a uremic solute concentration in a peritoneal dialysate removed from a patient measured by one or more uremic solute sensors (109) and a volume of peritoneal dialysate removed from the patient measured by one or more flow sensors (108) in a catheter; and
calculating a diffusion coefficient during a peritoneal dialysis dwell period based on data received from at least one glucose sensor during the same peritoneal dialysis dwell period; wherein the data received from the at least one glucose sensor is a glucose concentration in a portion of peritoneal dialysate removed from the patient during the peritoneal dialysis dwell period.

14. The method of claim 13, further comprising a step of calculating a dialysis adequacy using an equation Kt/V; wherein K is equal to clearance, t is time, and V is a patient water volume.

15. The method of claim 13 or 14, wherein the clearance is calculated by an equation clearance=$F/P \times L$, wherein F is the uremic solute concentration in the peritoneal dialysate removed from the patient, P is a blood uremic solute concentration of the patient, and L is the volume of peritoneal dialysate removed from the patient.

16. The method of claim 15, wherein P is calculated using an equation P=$F/(T \times D)$, wherein T is a time point during a peritoneal dialysis cycle and D is the diffusion coefficient for the patient.

17. The method of claim 16, further comprising a step of estimating a peritoneal membrane transport capability for the patient using an osmotic agent sensor in the catheter, a fluid line fluidly connectable to the catheter, or a reservoir fluidly connectable to the catheter.

18. The method of claim 15, wherein the uremic solute concentration of the peritoneal dialysate is measured at an end of a peritoneal dialysis cycle, and wherein P is calculated using an equation P=total uremic solute/V; wherein the total uremic solute is calculated using an equation total uremic solute=$F*L+F*(V-UF)$, wherein UF is an ultrafiltration volume for the peritoneal dialysis cycle.

19. The method of claim 13, wherein the uremic solute concentration in the peritoneal dialysate is measured with the one or more uremic solute sensors (109) in the catheter, a fluid line (107) fluidly connectable to the catheter, or a reservoir (112) fluidly connectable to the catheter.

20. The method of claim 13, further comprising a step of calculating a Kt/V from residual kidney function.

21. The method of claim 20, wherein the Kt/V from residual kidney function is calculated using an equation Kt/V from residual kidney function=$U/P \times L_u/V$, wherein U is a uremic solute concentration in urine of the patient and $L_u$ is a volume of urine produced.

22. The method of claim 20, further comprising a step of calculating a total Kt/V for the patient using an equation total Kt/V is equal to Kt/V from dialysis and Kt/V from residual kidney function.

23. The method of claim 13, wherein the step of calculating the clearance is performed by a processor of a peritoneal dialysis system.

24. The method of claim 13, wherein the uremic solute is selected from the group consisting of urea, creatinine, beta-2 microglobulin, uric acid, and combinations thereof.

* * * * *